(12) United States Patent
Haynie

(10) Patent No.: US 9,932,443 B2
(45) Date of Patent: Apr. 3, 2018

(54) PEPTIDE-BASED MATERIALS

(71) Applicant: Donald T Haynie, Tampa, FL (US)

(72) Inventor: Donald T Haynie, Tampa, FL (US)

(73) Assignee: University of South Florida, Tampa, FL (US)

(*) Notice: Subject to any disclaimer, the term of this patent is extended or adjusted under 35 U.S.C. 154(b) by 166 days.

(21) Appl. No.: 14/561,413

(22) Filed: Dec. 5, 2014

(65) Prior Publication Data

US 2016/0159981 A1    Jun. 9, 2016

(51) Int. Cl.

| C07K 14/78 | (2006.01) |
| A01N 37/18 | (2006.01) |
| C08G 69/14 | (2006.01) |
| C08G 69/16 | (2006.01) |
| C08J 5/00 | (2006.01) |
| C08J 9/00 | (2006.01) |
| C09D 177/02 | (2006.01) |
| C08J 5/18 | (2006.01) |
| C08L 89/00 | (2006.01) |
| D01F 4/00 | (2006.01) |
| D01F 6/68 | (2006.01) |
| C09D 177/04 | (2006.01) |
| C08G 69/10 | (2006.01) |
| D01D 5/00 | (2006.01) |

(52) U.S. Cl.
CPC ............ *C08G 69/14* (2013.01); *A01N 37/18* (2013.01); *C08G 69/10* (2013.01); *C08G 69/16* (2013.01); *C08J 5/00* (2013.01); *C08J 5/18* (2013.01); *C08J 9/00* (2013.01); *C08L 89/00* (2013.01); *C09D 177/02* (2013.01); *C09D 177/04* (2013.01); *D01F 4/00* (2013.01); *D01F 6/68* (2013.01); *C08J 2377/02* (2013.01); *C08J 2389/00* (2013.01); *D01D 5/003* (2013.01)

(58) Field of Classification Search
CPC ...... C09D 177/04; C09D 177/02; C07K 5/07; C07K 14/78; A01N 37/18; C08G 69/10; C08G 69/14; C08G 69/16; C08J 2377/02; C08J 2389/00; C08J 5/00; C08J 5/18; C08J 9/00; C08L 89/00; D01D 5/003; D01F 4/00; D01F 6/68; C08K 5/07
USPC .................. 521/183; 524/606, 607; 525/432; 528/323, 325; 514/21.3, 1.1; 530/300, 530/324, 353
See application file for complete search history.

(56) References Cited

U.S. PATENT DOCUMENTS

2014/0364371 A1* 12/2014 Setton .................. A61K 9/0024
514/16.8

FOREIGN PATENT DOCUMENTS

WO    WO 2014014613 A2 *  1/2014 ............. C07K 14/78

OTHER PUBLICATIONS

Haynie et al., "Mechanisms of Stability of Fibers Electrospun from Peptides with Ionized Side Chains," from Macromolecular Materials and Engineering, 2013, 298, pp. 529-540.*
Huang et al., "Generation of Synthetic Elastin-Mimetic Small Diameter Fibers and Fiber Networks," Macromolecules, 2000, 33:2989-2997.*
Acharya et al., "Refined structure of baboon α-lactalbumin at 1•7 Å resolution: comparison with C-type lysozyme," *Journal of Molecular Biology*, 1989, pp. 99-127, vol. 208, No. 1.
Aliferis et al., "Living polypeptides," *Biomacromolecules*, 2004, pp. 1653-1656, vol. 5.
Berger et al., "Poly-L-proline," *Journal of the American Chemical Society*, Nov. 5, 1954, pp. 5552-5554, vol. 76.
Boal, D. (2012). Polymers. In *Mechanics of the Cell* (pp. 65-104). Cambridge, UK: Cambridge University Press.
Bray, "Large-scale manufacture of peptide therapeutics by chemical synthesis," *Nature Reviews: Drug Discovery*, Jul. 2003, pp. 587-593, vol. 2.
Cuff et al., "ProtEST: protein multiple sequence alignments from expressed sequence tags," *Bioinformatics*, 2000, pp. 111-116, vol. 16, No. 2.
Deming et al., "Chain initiation efficiency in cobalt-and nickel-mediated polypeptide synthesis," *Journal of American Chemical Society*, 2000, pp. 5710-5717, vol. 122, No. 24.
Elvin et al., "Synthesis and properties of crosslinked recombinant pro-resilin," *Nature*, Oct. 13, 2005, pp. 999-1002, vol. 437.
Fasman et al., "High molecular weight Poly-L-Proline: synthesis and physical-chemical studies," *Biopolymers*, 1963, pp. 3-14, vol. 1.
Fudge et al. "Molecular design of the α-keratin composite: insights from a matrix-free model, hagfish slime threads," *Proceedings of the Royal Society of London B*, 2004, pp. 291-299, vol. 271.
Gill et al., "Calculation of protein extinction coefficients from amino acid sequence data," *Analytical Biochemistry*, 1989, pp. 319-326, vol. 182.
Haynie et al., "Structural energetics of the molten globule state," *Proteins: Structure, Function, and Genetics*, 1993, pp. 115-140, vol. 16.
Haynie et al., "Physical properties of polypeptide electrospun nanofiber cell culture scaffolds on a wettable substrate," *Polymers*, 2012, pp. 1535-1553, vol. 4.
Haynie et al., "Mechanisms of stability of fibers electrospun from peptides with ionized side chains," *Macromolecular Materials and Engineering*, 2013, pp. 529-540, vol. 298.
Haynie et al., "Polypeptide multilayer films: role of molecular structure and charge," *Langmuir*, 2004, pp. 4540-4547, vol. 20, No. 11.
Haynie et al., "Biomimetic nanostructured materials: inherent reversible stabilization of polypeptide microcapsules," *Langmuir*, 2005, pp. 1136-1138, vol. 21, No. 3.

(Continued)

*Primary Examiner* — Julie Ha
(74) *Attorney, Agent, or Firm* — Saliwanchik, Lloyd & Eisenschenk

(57) ABSTRACT

The subject invention pertains to peptide-based materials comprising cross-linked peptides with random amino acid sequences that are soluble in water or ethanol before cross-linking but insoluble in water after crosslinking.

15 Claims, 17 Drawing Sheets

(56) References Cited

OTHER PUBLICATIONS

Hsin et al., "Molecular origin of the hierarchical elasticity of titin: simulation, experiment, and theory," *Annual Review of Biophysics*, 2011, pp. 187-203, vol. 40.

Khadka et al., "A synthetic polypeptide electrospun biomaterial," *ACS Applied Materials & Interfaces*, 2011, pp. 2994-3001, vol. 3.

Khadka et al., "Insoluble synthetic polypeptide mats from aqueous solution by electrospinning," *ACS Applied Materials & Interfaces*, Sep. 2010, pp. 2728-2732, vol. 2, No. 10.

Khadka et al., "Protein- and peptide-based electrospun nanofibers in medical biomaterials," *Nanomedicine: Nanotechnology, Biology, and Medicine*, 2012, pp. 1242-1262, vol. 8.

Kim et al., "Crystallization of poly(L-proline) in the course of polymerization," *Makromolekulare Chemie*, 1979, pp. 465-472, vol. 180.

Wang et al., "Electrospinning of polymeric and ceramic nanofibers as uniaxially aligned arrays," *Nano Letters*, 2003, pp. 1167-1171, vol. 3, No. 8.

Linke et al., "Nature of PEVK-titin elasticity in skeletal muscle," *Proceedings of the National Academy of Science USA*, Jul. 1998, pp. 8052-8057, vol. 95.

Lu et al., "Hexamethyldisilazane-mediated controlled polymerization of α-amino acid N-carboxyanhydrides," *Journal of the American Chemical Society*, 2007, pp. 14114-14115, vol. 129. No. 46.

Nagapudi et al., "Photomediated solid-state cross-linking of an elastin-mimetic recombinant protein polymer," *Macromolecules*, 2002, pp. 1730-1737, vol. 35, No. 5.

Lyu et al., "Side chain contributions to the stability of alpha-helical structure in peptides," *Science*, Nov. 2, 1990, pp. 669-673, vol. 250, No. 4981, American Association for the Advancement of Science.

Osaki, "Spider silk violin strings with a unique packing structure generate a soft and profound timbre," *Physical Review Letters*, 2012, pp. 154301-154306, vol. 108, No. 15.

Peng et al., "Length-dependent prediction of protein intrinsic disorder," *BMC Bioinformatics*, Apr. 17, 2006, pp. 1-17, vol. 7, No. 208.

Peng et al., "Optimizing long intrinsic disorder predictors with protein evolutionary information," *Journal of Bioinformatics and Computational Biology*, 2003, pp. 1-23.

Peng et al., "Preparation of polypeptide via living polymerization of Z-Lys-NCA initiated by platinum complexes," *Macromolecules*, 2008, pp. 3455-3459, vol. 41, No, 10.

Petka et al., "Reversible hydrogels from self-assembling artificial proteins," *Science*, Jul. 17, 1998, pp. 389-392, vol. 281.

Regan et al., "Characterization of a helical protein designed from first principles," *Science*, Aug. 19, 1988, pp. 976-978, vol. 241.

Romero et al., "Sequence complexity of disordered protein," *Proteins: Structure, Function, and Genetics*, 2001, pp. 38-48, vol. 42.

Shen et al., "Stress-strain experiments on individual collagen fibrils," *Biophysical Journal*, Oct. 2008, pp. 3956-3963, vol. 95, No. 8.

Tan et al., "Tensile testing of a single ultrafine polymeric fiber," *Biomaterials*, 2005, pp. 1453-1456, vol. 26.

Tanford et al., "Proteins as random coils: I. intrinsic viscosities and sedimentation coefficients in concentrated guanidine hydrochloride," *Journal of the American Chemical Society*, Feb. 15, 1967, pp. 729-736, vol. 89, No. 4.

Thayer, "Making peptides at large scale," *Chemical & Engineering News*, May 30, 2011, pp. 21-25, vol. 89, No. 22.

Urry et al., "Mechanisms of elastin: molecular mechanism of biological elasticity and its relationship to contraction," *Journal of Muscle Research and Cell Motility*, 2002, pp. 543-559, vol. 23.

Van Beek et al., "The molecular structure of spider dragline silk: folding and orientation of the protein backbone," *Proceedings of the National Academy of Science USA*, Aug. 6, 2002, pp. 10266-10271, vol. 99, No. 16.

Vincent et al., "Design and mechanical properties of insect cuticle," *Arthropod Structure & Development*, 2004, pp. 187-199, vol. 33.

Weis-Fogh et al., "New molecular model for the long-range elasticity of elastin," *Nature*, Aug. 15, 1970, pp. 718-721, vol. 227.

Wetlaufer et al., "Control of aggregation in protein refolding: a variety of surfactants promote renaturation of carbonic anhydrase II," *Protein Science*, 1995, pp. 1535-1543, vol. 4, Cambridge University Press, USA.

Wimley et al., "Solvation energies of amino acid side chains and backbone in a family of host-guest pentapeptides," *Biochemistry*, 1996, pp. 5109-5124, vol. 35, No. 16.

Xue et al., "PONDR-FIT: a meta-predictor of intrinsically disordered amino acids," *Biochimica et Biophysica Acta Proteins and Proteomics*, 2010, pp. 996-1010, vol. 1804.

Zhang et al., "Context dependence of the assembly, structure, and stability of polypeptide multilayer nanofilms," *ACS Nano*, 2007, pp. 476-486, vol. 1, No. 5.

Zhang, "Fabrication of novel biomaterials through molecular self-assembly," *Nature Biotechnology*, Oct. 2003, pp. 1171-1178, vol. 21, No. 10.

\* cited by examiner

Solution synthesis
Non-uniform, polydisperse

Recombinant synthesis
Uniform, monodisperse

A                    B

Composition
○ 1/6
● 1/6
● 1/6
● 1/2

C

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: elastin-like peptides

<400> SEQUENCE: 1

Val Pro Gly Val Gly
1               5
```

PEPTIDE-BASED MATERIALS

BACKGROUND OF THE INVENTION

Synthetic polymer-based materials have played a vital role in modernization and thus advanced the quality of life for people everywhere (Nicholson, 2006). Humans have made extensive use of polymeric materials for at least 20,000 years, in the form of wood (polysaccharides) and animal furs, wools and silks (polypeptides); reliance on polymers cannot be expected to change soon. The scale of the need is global. Ideally, polymer production will also be renewable and sustainable. Based on current estimates, the USA can be energy-independent for perhaps 200 years. In order to be able transition at some point to alternative polymers for materials fabrication, however, alternatives must first be identified and developed in ways that make sense for manufacturing. In addition, alternatives may display novel or desirable properties that either cannot be realized, or are difficult to realize, with synthetic polymers.

The most common backbone atoms in synthetic polymers are carbon, hydrogen, and oxygen. Synthetic polymers such as plastic molded parts are currently in high demand because they are often stronger, lighter, less expensive or have a longer useful lifetime than wood or metal counterparts. Synthetic polymers, for example, are made into molded airplane parts and automobile components, disposable scientific labware, paints, glues, textiles, shoe parts, baby bottles, disposable supermarket packaging and a wide variety of other products. Nevertheless, the long-term future of synthetic materials is imperiled by fluctuations in the price of petrochemicals and the diminishing availability of precursors.

Two promising classes of alternative polymers are polysaccharides and polypeptides. Both are made naturally by living organisms. Although the roles of peptides in living organisms have been studied in great depth in the context of protein structure and function, the potential advantages of peptides for materials fabrication are still largely unknown.

A common classification scheme for proteins has three categories: membrane proteins, globular proteins and structural proteins (Voet et al., 2006). The last group is the most important one for alternative polymers for materials manufacturing. For example, some structural proteins found in spider dragline silk and mammalian connective tissue have a comparatively repetitive amino sequence and thus low sequence diversity. It is unclear, however, whether the same sequences are mostly A) products of an evolutionary optimization process for functional advantage or B) artifacts of loosely controlled gene duplication in which copies became tandem repeats in a single gene. One key hypothesis is that the amino acid composition of some structural proteins is as much a matter of gene duplication as random mutation and selection.

Previous studies of protein-based or -derived materials have produced interesting results and revealed remarkable properties. Spider silk, for example, is stronger than steel per unit mass (e.g. van Beek et al., 2002). Thousands of spider silk strands have been spun into a set of violin strings (Osaki, 2012). Current research focuses on wild-type polypeptides (endogenous or recombinant), wild-type-like polypeptides (recombinant) or structural elements based on wild-type polypeptides (recombinant or synthetic). Examples of the last category are elastin-like peptides (ELPs) and leucine zippers, which have been involved in studies on the elastic properties of biological tissues (elastin) and hydrogels for drug delivery (leucine zippers) (Urry and Parker, 2002; Petka et al., 1998). Elastin, though biodegradable, has a remarkably long half-life in vivo, where it undergoes millions of extensions and retractions over the lifetime of the organism.

Properties of elastin, resilin, wool keratins and other proteins suggest that materials made of designed polypeptides could display desirable elasticity, durability and biodegradability. It has long been assumed that the elasticity of the noted proteins is attributable to sequence, secondary structures and tertiary structures. However, certain regions of the proteins resilin and titin, for example, are known to play a crucial role in elasticity but comprise little secondary structure (Elvin et al., 2005; Hsin et al., 2011). Moreover, these regions have low amino acid sequence diversity.

The structure of every protein, including elastin and resilin, is assumed to have resulted from a long evolutionary selection process and thus to be optimized for functionality. Reverse-engineering what nature has already done, however, has two major drawbacks: First, random peptides are more similar than gene-encoded peptides to the synthetic polymers of materials manufacture, some of which have been unqualified successes. Proteins, in contrast, are essentially monodisperse, the sequences are essentially identical, and the chains tend to adopt specific secondary structures, $\alpha$ helices and $\beta$ sheets, to fold and display specific functions (Voet et al., 2006. Second, natural helices and sheets tend to be unstable apart from the rest of the protein (Finkelstein and Ptitsyn, 2002) and random amino acid sequences are unlikely to adopt stable secondary structures or show regular patterns of persistent hydrogen bonding. Nevertheless, stable secondary structures have been designed (e.g. Regan and DeGrado, 1988), and they could enhance properties of non-biological bulk peptide materials (e.g. Petka et al., 1998). Such successes have led investigators to believe that designed materials must contain such structures, as hydrogen bonds are believed to be significant contributors to protein thermostability (Finkelstein and Ptitsyn, 2002).

At ambient temperatures, bond vibrations in most molecules, including polymers, are limited (Strobl, 2007) and double bonds do not rotate. This has significant consequences for entropy and elasticity by way of limiting the number of accessible conformations to a polymer chain. In peptide bonds, backbone rotations are further limited by electron delocalization (Voet et al., 2006). One odd feature of the peptide backbone is the presence of nitrogen in the amino group, which is a hydrogen bond donor. This feature contributes to the polar nature of the polypeptide and has significant consequences for polymer solubility in water, intra-chain structure formation, inter-chain bonding and chain entropy.

Peptides can be synthesized by ring-opening polymerization, characterized in aqueous solution by gel permeation chromatography, viscometry, circular dichroism spectroscopy and other methods and processed into 1-, 2- and 3-dimensional materials by several guided self-assembly methods: electrospinning, film casting and molding, respectively. Mechanical properties of the materials can then be determined by uniaxial tensile strength testing and other methods. However, current peptide synthesis requires prior knowledge of sequence or persistent secondary or tertiary structure.

Linear homopolypeptides and heteropolypeptides, uniform and non-uniform sequence, respectively, can be prepared by solid-phase or solution-phase methods (chemical approaches) or recombinant methods (biological approaches). These synthesis approaches have advantages and disadvantages for different purposes. For example, chemical synthesis is advantageous for small-peptide biologics production. Solution-phase approaches are usually favored for therapeutic peptides shorter than 15 amino acid residues and quantities over 100 kg, whereas complex or longer sequences are usually made by solidphase synthesis, and peptides longer than 50 residues are made by recombinant methods (Thayer, 2011). All industrial enzymes are made by biological methods.

BRIEF SUMMARY OF THE INVENTION

The subject invention relates to a solution-phase synthesis of statistical peptides of defined composition for nanostructured materials fabrication. Based on the dependence of current manufacturing practices on petrochemicals, the limited future availability of petrochemicals, and the potential for sustainable production of polypeptides, the subject invention provides new means and methods of materials fabrication, which are useful for the assessment of the molecular basis of elasticity and for the development of peptide materials with novel functionality and utility.

In one aspect, the present invention provides a peptide-based material comprising cross-linked peptides with random amino acid sequences that are soluble in water or ethanol before crosslinking but insoluble in water after crosslinking.

In one embodiment, the random amino acid sequences are fused with one or more elastin-like peptides (ELPs). The peptide-based material may further comprise synthetic organic polymers.

In one embodiment, the cross-linked peptides utilized in the peptide-based materials of the invention are synthesized by ring-opening polymerization.

In some embodiments, the peptide-based material is a disposable material, such as, for example, a biodegradable material. In other embodiments, the material is a cell culture scaffolding material. In yet another embodiment, the peptide-based materials are foam materials.

In other embodiments, the peptide-based material can be either a one-dimensional, two-dimensional, or three-dimensional material. Such "one-dimensional" materials are fibers or fiber materials, such as, but not limited to, anti-microbial fiber materials. "Two-dimensional" materials are film materials, such as, but not limited to, medical device coating films. Three-dimensional materials may be molded materials.

Manufacturing instructions are potentially programmable in such polymers in that amino acid composition, DP and solution conditions determine polymer structure and interactions. A key aspect of the invention is its emphasis on water solubility. A distinctive feature of the invention is the use of peptides with random amino acid sequences for materials fabrication.

Randomness will have consequences for polymer chain behavior and thus material elasticity. Usual synthetic polymers are homopolymers or random co-polymers. Usual synthetic polymers form entropic networks. The polypeptides of this invention also can form entropic networks. Random peptides have not been studied before as discussed herein. In virtually all previous studies involving random peptides, sequences of wild-type proteins were scrambled to negate the possibility that functionality derived from composition rather than structure. Our primary concern here is not possible biochemical functionality, but rather our focus is mechanisms and characteristics of elasticity in peptide materials.

It is a premise underlying the instant invention that the mechanical properties of some proteins, especially elastomers, are a matter of amino acid composition rather than sequence.

The instant invention provides that the entropic elasticity of a material, and therefore the conversion of stored elastic energy to mechanical energy, is greatest when enthalpic contributions are minimized or at least controlled. The fact that regular hydrogen bond formation limits the randomness of chain conformations increases the significance of enthalpic contributions to elasticity. For example, the protein resilin displays a marked lack of secondary structure and a high level of conversion of elastic energy to mechanical energy (Elvin et al., 2005).

DETAILED DISCLOSURE OF THE INVENTION

Figure 1:
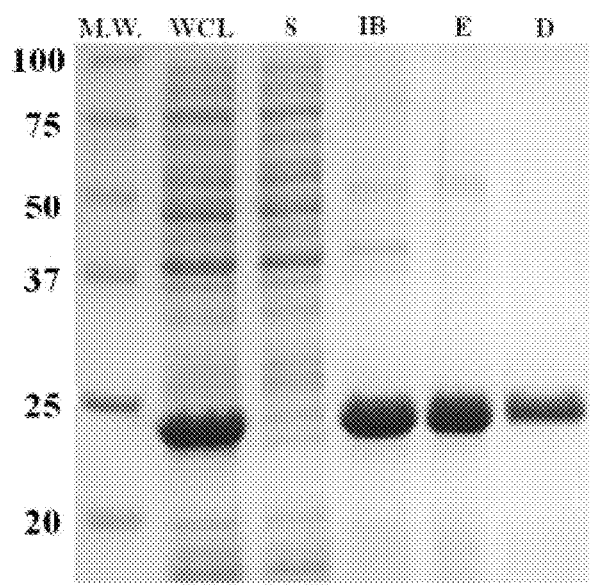
FIG. 1 shows expression and purification of a recombinant randomized ELP. M.W., ladder standard in kDa. The polymer has a calculated mass of 23.4 kDa, including His tag. WCL, whole-cell lysate. S, soluble fraction of lysate. IB, inclusion bodies. E, eluate from Ni-NTA column. D, dialysis retentate. The recombinant peptide thus processed had a final purity >90% by SDS-PAGE.
Figure 2:
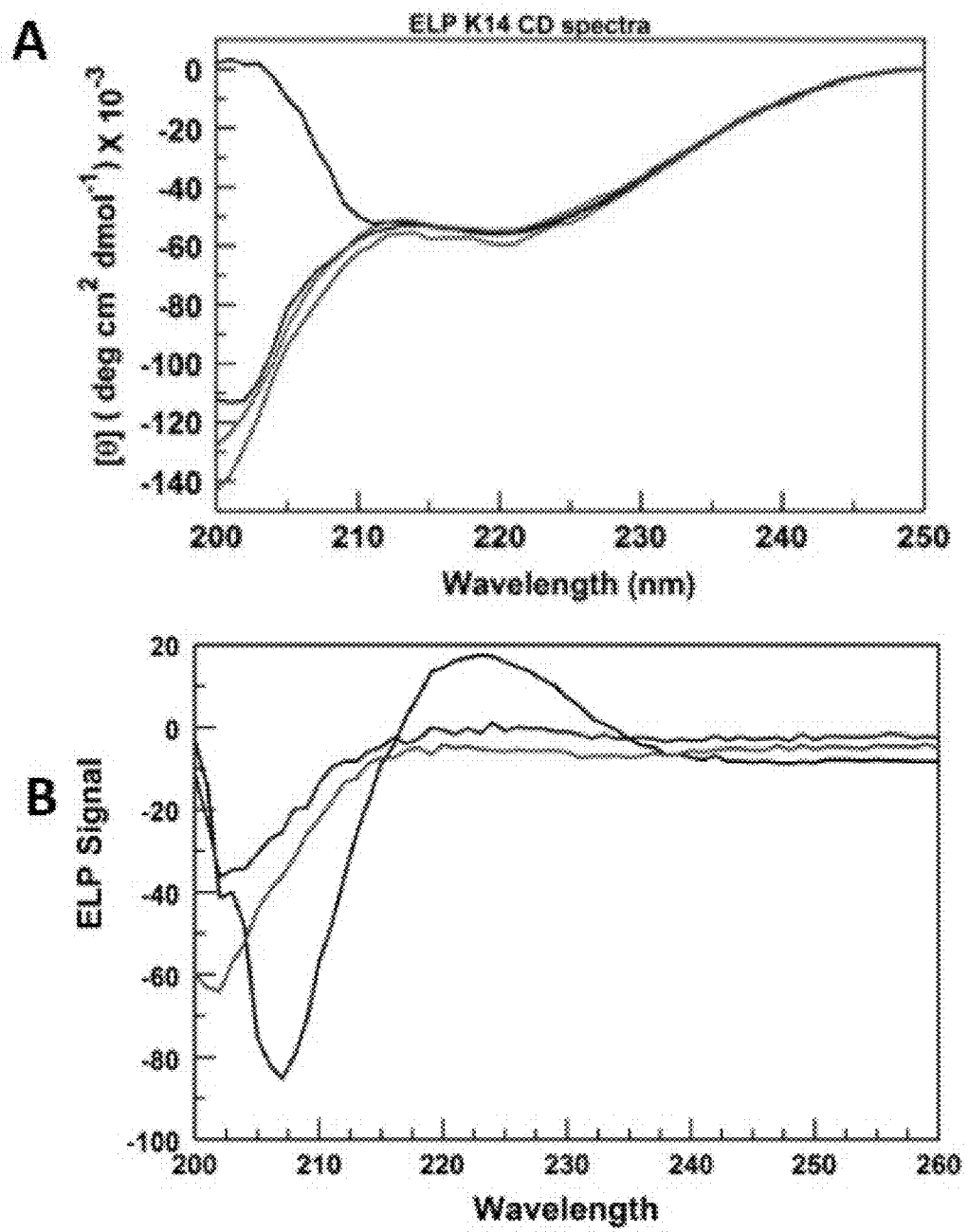
FIG. 2 shows preliminary analysis of polymer structure in solution by far-UV circular dichroism spectroscopy. A) K14 at different concentrations in DI water. There is clear evidence for β spiral. Black, blue, green and red color lines represent nominal polymer concentrations of 0.125, 0.063, 0.031 and 0.017 mg/mL, respectively. Other concentrations were not tested. After solvent baseline subtraction, the spectra were normalized for molar concentration of polymer, determined in each case by UV absorbance, and converted to molar ellipticity $[\theta]=3300\Delta A/cl$, where $\Delta A$ is the measured differential absorbance, c is the molar concentration of polymer and l is the light path length. B) Randomized ELP (black) and K14-keratins (blue and red) at 0.0625 mg/mL in water. Evidence for β spiral is lacking. The randomized ELP spectrum looks random coil-like. The K14-keratin spectra look like the short-wavelength region of the spectra in A). The solvent baseline has been subtracted out but the spectra have not been converted to ellipticity or normalized for concentration.

Aspects of the present invention relate to solution-phase synthesis of statistical peptides of defined composition for nanostructured materials fabrication. In specific embodiments, the subject invention provides a method for synthesizing protein-inspired random peptides to assess the limits of elasticity of materials made of these peptides by way of systematic variation of molecular design. In other embodiments, the subject invention provides peptides having random amino acid sequences that are soluble in water or ethanol before crosslinking but insoluble in water after crosslinking. In particular embodiments, the subject peptides "exhibit" high elasticity.

Evidence supporting the structural and functional potential of unexplored polypeptide materials is provided by the remarkable variety of three-dimensional structures, biochemical functionalities and physical properties displayed by known natural proteins on the one hand and the astronomical number of possible amino acid sequences on the other hand. The genetic interrelatedness of all known biological organisms, combined with the need for non-lethal mutations for future generations, seems to have greatly limited the exploration of amino acid sequence space, not advanced it. The number of possible chemically distinct amino acid sequences is absolutely vast. The 20 usual amino acids alone can potentially be made into $20^{100} \approx 10^{131}$ different chains 100 units long—smaller than the average peptide in any cell. The age of the universe, by contrast, is only $10^{18}$ seconds old, and the total number of protons is about $10^{80}$. This is sufficient proof that only a very tiny fraction of possible sequences has been studied. All peptide and protein research to date, therefore, though informative, has but scratched the surface of what can be known about peptides for materials.

Polypeptides are useful in strong, lightweight, functional and elastic materials. Examples of natural polypeptides include spider silk and muscle proteins. Embodiments of the subject invention can improve on such natural polypeptides in certain respects. Textiles, medical materials and disposable materials are included in areas of application for peptide materials. These materials can provide superior performance with regard to elasticity, energy conversion efficiency, strength per unit mass, biodegradability and foreign body tissue reactions. In addition, compared to synthetic polymers, polypeptides—especially designed peptides—can be made sustainably. This is a feature that can be particularly useful in the field of advanced manufacturing.

In an embodiment, the subject invention provides manufacturing instructions regarding amino acid composition, degree of polymerization (DP) and solution conditions, which determine polymer structure and interactions. In some embodiments, the polypeptide processing is performed at ambient temperature under mild solution conditions, and the materials are biodegradable.

In some embodiments, peptide polymers are water soluble and the amount of organic solvent needed in materials manufacturing is reduced or eliminated. In further embodiments, the random polypeptides are soluble in water and/or ethanol before crosslinking but insoluble in water after crosslinking.

Additional aspects relate to the use of peptides with random amino acid sequences for materials fabrication. The randomness embodied in the subject invention provides the ability to simultaneously make the synthetic peptides less like native globular proteins and more like the usual synthetic polymers in materials manufacturing and key regions of elastomeric proteins, such as for example, titin and resilin.

In one aspect, the present invention provides a peptide-based material comprising cross-linked peptides with random amino acid sequences that are soluble in water or ethanol before crosslinking but insoluble in water after crosslinking. In one embodiment, the random amino acid sequences are fused with one or more elastin-like peptide (ELP). The peptide-based material may further comprise synthetic organic polymers. In some embodiments, the cross-linked peptides utilized in the peptide-based materials of the invention are synthesized by ring-opening polymerization.

In some embodiments, the peptide-based material can be either a one-dimensional, two-dimensional, or three-dimensional material. Such one-dimensional materials are fiber materials, such as, but not limited to, anti-microbial fiber materials. Two-dimensional materials are film materials, such as, but not limited to, medical device coating films. Three-dimensional materials are molded materials.

In one embodiment, the polypeptides of the subject invention form entropic networks. The skilled artisan can appreciate that the materials of the subject invention, although random peptides, are nevertheless at least potentially hybrids of structure and function, not just one or the other.

In some embodiments, the subject invention provides fusion peptides consisting of structural parts based on the present invention and functional parts based on biochemical research.

In some embodiments, the subject invention provides a method for synthesizing statistical, linear peptides in solution based on ring-opening polymerization of α-amino acid N-carboxyanhydrides, wherein growth occurs only by the probabilistic addition of monomers to active chain ends. In further embodiments, monomers are present throughout the process and polymer mass and yield are functions of mechanism and reaction particulars. In some embodiments, the product has a Poisson distribution of chain lengths, $(\tilde{N}e/N)^N \exp(-\tilde{N})$, where N is DP and $\tilde{N}$ is number-average DP, and N can range from 2 to >2,000. In some embodiments, short-range order is possible, long-range order is improbable and the synthesis from a heterogeneous monomer population is expected to yield chains of virtually identical amino acid composition.

The subject invention is especially advantageous if monodisperse polymers and sequence specificity are optional and amino acid composition, predictability of water solubility, measurability of number-average mass and weight-average molecular mass, and therefore polydispersity index, and reproducibility of polymer production materials processing are desired.

In some embodiments, the subject invention provides control of polydispersity by reaction conditions and fractionation.

In some embodiments, the subject invention provides a blend of different recombinant random sequences useful for material properties. In specific embodiments, the peptides are produced at high yield in photosynthetic bacteria.

In other embodiments, the subject invention provides a solution-phase approach for random peptide production. The peptide polymers of the subject invention are polydisperse and have a low predicted crystallinity.

In some embodiments, the subject invention provides electrospun fibers, including Poly(L-ornithine) (PLO), PLEY, PLL and Poly(L-glutamic acid) (PGLA).

In additional embodiments, the subject invention provides elastin-like peptides (ELPs) [(VPGVG)n] ([(SEQ ID NO:1) n]). In further embodiments, the ELPs are spinnable from water. The subject invention further provides peptides of a mole fraction of glutamic acid of 0.8-1.0, which corresponds to a maximum absolute value of average charge density for electrospinning from aqueous solution at pH 7.

In some embodiments, the subject invention provides cast films, molded materials and foams. In further embodiments, the cast films and molded materials are made water-insoluble by cross-linking.

In additional embodiments, the subject invention provides an algorithm that relates elasticity and other aspects of materials processing to amino acid composition, degree of polymerization, pH, hydration and ionic strength.

In some embodiments, the subject invention relates to the use of circular dichroism (CD) spectroscopy to analyze structural properties of peptides during multilayer film buildup.

In other embodiments, the subject invention relates to the visualization of electrospun fibers by fluorescent microscopy.

In yet other embodiments, the subject invention relates to the use of a visible-range dye to quantify the efficiency of peptide crosslinking, wherein the decrease of dye absorbance is a measure of the increased concentration of cross-linked polymers.

In further embodiments, the subject invention provides the use of energy-dispersive X-ray spectroscopy to measure the presence of counterions in peptide fibers, wherein the rate of annealing by irradiation is measured as a function of counterions leaching out of cross-linked fibers.

Peptide Synthesis for Materials Manufacturing

This invention focuses on peptides for making materials. Characterizing peptide-based materials and determining relationships between polymer structure and solution and material properties matter most here. The scalability of polymer synthesis and materials manufacture; convenience; cost of synthesis and purification; and limitations on polymer structure are important.

Figure 3:
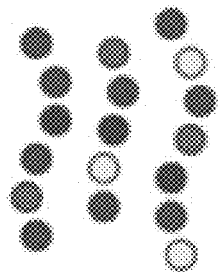
FIG. 3 shows comparison of the products of solution synthesis and recombinant synthesis for chains longer than about 15 residues. The amino acid composition is constant. Solution synthesis results in a non-uniform population of polymers; sequence and chain length are random variables within the same synthesis product. Recombinant synthesis yields uniform populations of polymers. Specific examples A, B and C of pre-selected random sequences are shown. Amino acid monomers were selected at random for a target composition, and the sequences were encoded in genes.
Figure 3:
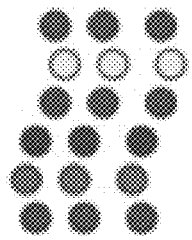
Figure 3:
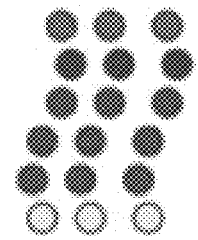
Figure 3:
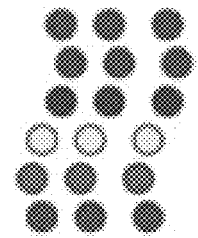

Linear homopolypeptides and heteropolypeptides, uniform and non-uniform sequence, respectively, can be prepared by solid-phase or solution-phase methods (chemical approaches) or recombinant methods (biological approaches) (see FIG. 3). These synthesis approaches have advantages and disadvantages for different purposes. For example, chemical synthesis is advantageous for small-peptide biologics production. Solution-phase approaches are usually favored for therapeutic peptides shorter than 15 amino acid residues and quantities over 100 kg, whereas complex or longer sequences are usually made by solid-phase synthesis, and peptides longer than 50 residues are made by recombinant methods (Thayer, 2011). All industrial enzymes are made by biological methods.

Ring-opening polymerization of α-amino acid N-carboxyanhydrides, the main approach to synthesizing peptides in solution, is utilized herein. The method yields statistical, linear polypeptides. Growth occurs only by the probabilistic addition of monomers to active chain ends. Monomers are present throughout the process, but their concentration falls with time. Polymer mass and yield are functions of mechanism and other reaction particulars. The product will normally have a Poisson distribution of chain lengths, $(\tilde{N}e/N)$ $N\exp(-\tilde{N})$, where N is degree of polymerization (DP) and $\tilde{N}$ is number-average DP (Strobl, 2007). N can range from 2 to >2,000. Short-range order is possible; long-range order, improbable. Synthesis from a heterogeneous monomer population is expected to yield chains of virtually identical amino acid composition. The approach is advantageous if monodisperse polymers and sequence specificity are optional. Polydisperse co-poly(L-glutamic acid4, L-tyrosine 1) (PLEY), a random copolymer, has been studied (Khadka et al., 2011; Haynie et al., 2012; Haynie et al., 2013).

Solution-phase production of a monodisperse population of polypeptides of identical sequence is not only possible but actually done in industry. It is very expensive, however, if the DP is greater than about 15 residues. Solid-phase synthesis of sequence-specific polypeptides is even more expensive per unit mass. DP is practically limited to about 50 residues, as yield decreases with chain length. Double coupling can improve the efficiency of monomer addition at each step and the yield of desired product, albeit at a cost. Consequently, peptides made by chemical methods cannot be competitive in the marketplace unless consumers are willing to pay a premium. In general terms, sequence specificity by chemical production is too expensive except for limited purposes in medicine, basic research and defense (see Bray, 2003).

The functional properties of proteins are "microscopic" in that they typically depend on amino acid sequence. For instance, enzyme activity requires appropriate positioning of chemical groups. The physical properties of polymer aggregates, by contrast, are "macroscopic." Such properties could depend on amino acid sequence as much as composition. Perhaps the most positive way of regarding solution-phase synthesis of peptides in a materials context is to focus on cases in which it is certain that sequence will be less relevant than a) amino acid composition, b) predictability of water solubility, c) measurability of number-average mass and weight-average molecular mass and therefore polydispersity index and d) reproducibility of polymer production and materials processing. Chemical composition, average DP and, to a lesser extent, polydispersity index may be treated as essentially continuous and independent variables, and the systematic investigation of relationships between polymer structure and materials will be possible.

Chemical synthesis, it should be acknowledged, presents both advantages and disadvantages. The plus side features ease of polymer preparation and latitude with regard to composition. A potential advantage for materials is the incorporation of unusual amino acids, which proceeds in essentially the same way as for a usual amino acid. The main limitations are the prohibitive cost of controlling sequence. For this subject invention, however, specific sequences are not needed. Polydispersity can be controlled by reaction conditions and fractionation. Side chain protecting groups can influence polymerization, but the final amino acid composition of products can be measured. Incomplete removal of protecting groups after synthesis can influence downstream processing, but the abundance of such groups can be quantified. How material properties depend on a lack of sequence uniformity or polydispersity can be tested by recombinant production of monodisperse peptides of identical composition.

Recombinant production will in any case have unique and complementary advantages to solution-phase synthesis for materials research and possible technology commercialization. If control over amino acid composition, sequence and polydispersity are required at any scale of production, if the ability to encode manufacturing instructions into polymer structure requires sequence specificity, and if there is no need to guarantee freedom from small amounts of bacterial contaminant, then recombinant production could be the least expensive approach to synthesis. Peptide purity of >95% is readily and reliably achieved, and polymers of substantially greater purity can be obtained without great difficulty. Systematic variation of amino acid composition is more difficult than for solution-phase synthesis, as at least one gene is needed per polymer structure, but it can be done by established and cost-effective methods. A small number of representative random sequences of a given amino acid composition and chain length could be made by recombinant methods and compared experimentally. A blend of different recombinant random sequences can prove useful for material properties. Biological peptide production is also potentially significant for sustainable manufacturing. Production in photosynthetic bacteria can be especially advantageous for the purpose; high yields of recombinant proteins have been obtained in photosynthetic bacteria.

One approach to peptide synthesis and processing could be more advantageous for some amino acid compositions than others. Recombinant synthesis may be best for protein-like sequences, that is, ones for which the composition resembles the average composition of proteins. Whether a solution-phase approach or a recombinant approach for random peptide production is best for large-scale production depends on the cost of polymer production, characterization and processing, and the desirability of the physical, chemical or biological properties displayed by materials that can actually be made with a polypeptide of a given sequence or composition.

Structural Requirements of Peptides for the Materials of this Invention

A major criterion for materials of the invention is polymer solubility in water. The present invention requires water solubility for polymer synthesis, materials processing and materials performance. Embodiments of the invention utilize random polypeptides of known amino acid composition. What follows concerns structural requirements of peptides for embodiments of the invention.

material. PLL, for instance, is not spinnable, but it is useful for cast films and molded materials (see below). Cast films of PLEY have been made and analyzed (Khadka et al., 2011). PLL and PLEY may also be useful in foams. It is probable but not certain that every spinnable polymer will also be suitable for making the other materials of interest herein. The converse is apparently not true for the reasons noted above. Cast films can be set and made water-insoluble by crosslinking

TABLE 1

Some amino acids relevant to the proposed study

| Species | Lysine | Ornithine | Glutamic acid | Aspartic acid | Tyrosine |
|---|---|---|---|---|---|
| Codes | Lys, K | Orn, O | Glu, E | Asp, D | Tyr, Y |
| Form | Zwitterion, ionized side chain | Neutral | Neutral | Neutral | Neutral |
| Structure | | | | | |

1-Dimensional Materials

Electrospun fibers are among the materials described herein. Poly(L-ornithine) (PLO), PLEY, PLL and poly(L-glutamic acid) (PLGA) are described. All are highly ionized and highly soluble in water (>10 mg/mL), but only PLO and PLEY are spinnable at any average DP, concentration, pH and ionic strength (Khadka and Haynie, 2010; Khadka et al., 2011; Haynie et al., 2012; Haynie et al., 2013; unpublished data). Therefore, solubility does not necessarily imply spinnability, even at high concentrations of polymer. ELPs [(VPGVG)n] ([(SEQ ID NO:1)n]) are remarkably water-soluble, even at molecular masses >100 kDa, despite the lack of ionizable side chains. The large dipole moment of the peptide bond dominates over the hydrophobicity of valine (V) in aqueous solution. ELP is spinnable from water (Nagapudi et al., 2002; preliminary results).

The lower limit on the average linear charge density for peptide spinnability from aqueous solution is zero, and if a charge density threshold is exceeded, the polymer will not be spinnable (assuming a DP criterion). PLL and PLGA exceed the threshold at pH 7 but PLO and PLEY do not. PLO, despite its similarity to PLL, has a lower charge density at pH 7, due to a greater repulsion between ionized side chains; the side-chain amino groups are closer to the polymer backbone than in PLL and thus closer to each other (Table 1). Few tyrosine side chains in PLEY will be ionized at pH 7 (nominal $pK_a$>10; Dawson et al., 1986). The higher charge on PLL or PLGA will give these polymers a longer persistence length than PLO or PLEY. Because PLEY is 80% glutamic acid, the electrospinning data suggest that the maximum absolute value of the average charge density on peptides for electrospinning from aqueous solution at pH 7 corresponds to a mole fraction of glutamic acid of 0.8-1.0. This result provides a foundation for some of the embodiments of the invention described herein.

2-Dimensional Materials

Other materials of interest herein are cast films. Polypeptide processing requirements will depend on the type of

3-Dimensional Materials

Molded materials can apparently be formed from the broadest range of amino acid compositions. Molded materials can be set by polymer crosslinking (see Examples).

Polymer Crosslinking

Polymer crosslinking influences the elasticity of polymeric materials by reducing the effective length of individual chains and increasing the interactions between chains. Elastin and resilin are highly cross-linked peptide elastomers. The structural integrity of materials made of soluble peptides can be influenced by crosslinking, as a cross-linked polymeric material is essentially a single giant macromolecule and less soluble than a multitude of individual polymer chains. Three approaches have been selected for embodiments herein. All are well established. The most appropriate approach is a function of polymer design. 1) Diimide crosslinking requires both free carboxylate groups and free amino groups. EDC has been utilized to crosslink PLEY in electrospun fibers, alone and in blends with ELP, and quantified the efficiency of the process (Khadka et al., 2011; Haynie et al., 2012; see Examples). 2) Aldehyde crosslinking requires free amino groups. Glutaraldehyde has been utilized to crosslink PLO in electrospun fibers and PLL in molded materials (Khadka and Haynie, 2010; see Examples). 3) Disulfide crosslinking requires free sulfhydryl groups. Oxidizing conditions have been utilized to crosslink cysteine-containing peptides in multilayer films and to study the decay of disulfide-cross-linked materials in a reducing environment (Li and Haynie, 2004; Haynie et al., 2005). Details are provided in the Materials and Methods section herein.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Materials and Methods

Prediction of Polymer Properties.

Nominal $pK_a$ values are from Dawson et al. (1986). Actual values in polypeptides can be somewhat different but large deviations are not expected. The values are used to estimate the net charge on peptides at pH 7 and interpret experimental data (e.g. polymer solubility).

Accessible surface areas of peptides are calculated as in Wimley et al. (1996). The reported values were obtained by computational methods for the side chain and backbone of all 20 usual amino acids. These quantities are used to calculate the polar and non-polar surface areas of each polymer design following analysis of amino acid composition and chain length (see below).

Secondary structure is predicted as in Cuff et al. (2000). TBLASTN compares the query sequence (length n) with the EMBL-Expressed Sequence Tag (EST) database. The entire sequence of any identifier with a p-value $\leq 10^{-4}$ is retrieved from the EMBL-EST database. All retrieved sequences are clustered, assembled, and compared and queried with ProtESTWise and ESTWISE. Sequence lengths <2n/3 are discarded and >3n/2 are shortened at the ends. Sequences with >3% errors are discarded. BLASTP is then used to search the SWISS-PROT database. The EST sequences are combined with the BLASTP results, clustered and aligned with CLUSTALW. The needed software is available online. The intrinsic disorder of designed peptides is predicted with the algorithms PONDR® VLXT (Romero et al., 2001), PONDR® VSL2 (Peng et al., 2005), PONDR® VL3 (Peng et al., 2006) and PONDR® FIT (Xue et al., 2010). VLXT uses 3 neural networks, one for each terminal region and one for the internal region of a test sequence. Each network is trained by a dataset containing only the amino acid residues of the corresponding region. The final prediction combines the individual predictions. VL3 employs 10 neural networks; the final prediction is made by majority voting. VL3 is especially suited for long disordered regions, >30 amino acid residues. VSL2 combines neural network predictors of short and long disordered regions. Each predictor is trained by the dataset containing sequences of the corresponding length. The final prediction is a weighted average. FIT, a consensus neural network predictor, combines the results of PONDR® VLXT, PONDR® VSL2, PONDR® VL3, FoldIndex, IUPred and TopIDP to give a more accurate result than its components. All needed software is available at USF.

In combination with experimental data for solution and material properties, the calculations can have significant predictive value. Whether the noted calculations, alone or combined, accurately model experimental properties of the subject materials is assessed. For ELP, for example, the known and predicted secondary structure in solution is compared, and the properties of ELP and random peptides of the same amino acid composition and DP as ELP; and the same for intrinsic disorder.

Polymer Synthesis.

Figure 11:
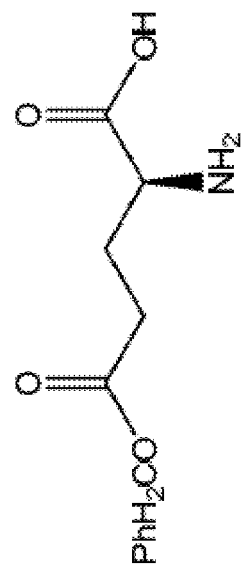
FIG. 11 is a schematic showing the synthesis of N-carboxyanhydride.
Figure 11:
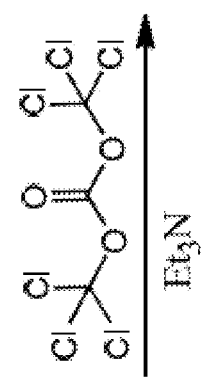
Figure 11:
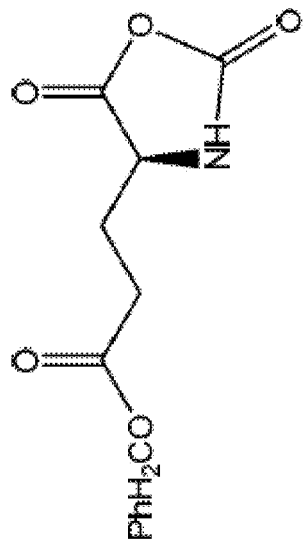

The peptides are made by synthesis of N-carboxyanhydrides (NCAs) (Berger et al., 1954; Fasman and Blout, 1963; Kim et al., 1979). Protected amino acids are reacted with solid triphosgene, and the resulting N-carbamoylchlorides are cyclized in the presence of base (FIG. 11). One-third equivalent of triphosgene is added to 10 grams of side chain-protected amino acids suspended in 100 mL of anhydrous tetrahydrofuran (THF) at 50° C. under Ar for 1-3 hours. If the solution has not clarified within 1 hour, 2 to 3 aliquots of triphosgene (0.05 equiv.) is added at 30 minute intervals, yielding a homogeneous solution of the NCA. After 3 hours, the reaction mixture is poured into 300 mL of hexane. The suspension is stored for 16-20 hours at −20° C. The precipitate is then removed by filtration. Crude NCA is vacuum dried overnight, purified by precipitation from a mixture of THF and a large excess of hexane, and crystallized from hot hexane. The process is repeated if analysis by IR, $^1H$ NMR or $^{13}C$ NMR spectroscopy should provide evidence of contamination. Pure NCA is stored in a glove box.

Figure 12:
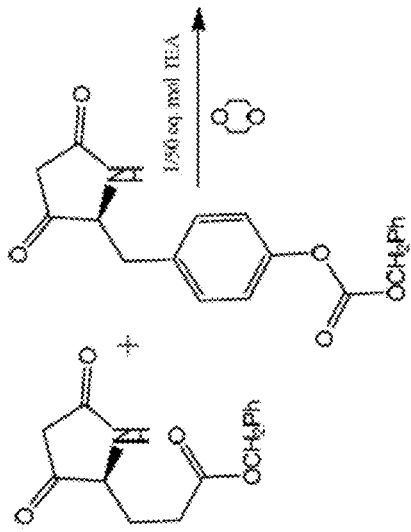
FIG. 12 is a schematic showing polypeptide synthesis (PLEY) by ring opening co-polymerization of N-carboxyanhydrides.
Figure 12:
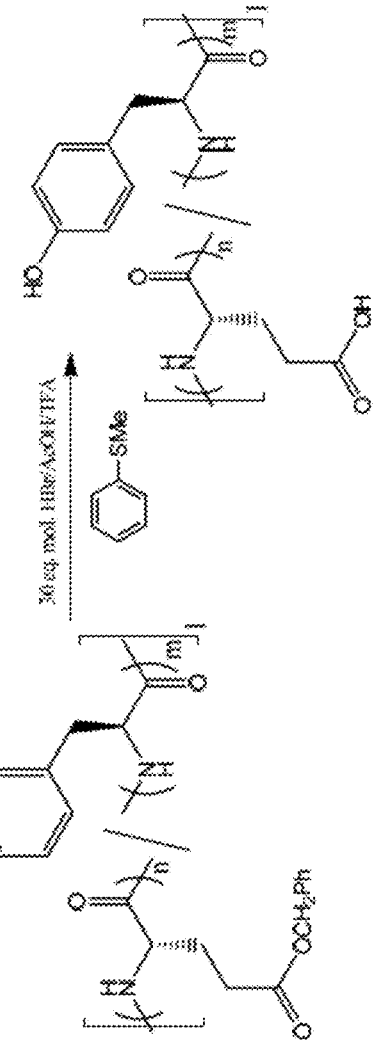

NCA polymerization has been a topic of some moment in research, product development and commercial activity. New initiators have recently been developed (Deming and Curtin, 2000; Peng et al., 2008; Lu and Cheng, 2007). Here, tertiary amines and high vacuum techniques are used for amino-initiated NCA polymerization (Aliferis et al., 2004). See FIG. 12. Amino acid-NCAs are vacuum dried in a flame-dried, specially-designed glass reactor. Freshly distilled solvent is introduced to dissolve the monomers. A triethylamine solution (A/I=100) is injected with vigorous stirring for a preset time with degassing of $CO_2$. The resulting polypeptide is precipitated in cold ether and dried in vacuo. Product purity is assessed by size-exclusion chromatography and FTIR, $^1H$ NMR and $^{13}C$ NMR spectroscopy. Co-polypeptides are deprotected in a trifluoroacetic acid/thioanisole mixture (1.0 molar equiv. of benzyloxy groups), yielding soluble peptides. 25% HBr in acetic acid (10 molar equiv. of protecting groups) is added with stirring. Aliquots of the reaction mixture is taken periodically to monitor protecting group removal. After c. 8 hours, the reaction mixture is evaporated at low pressure, and deprotected co-polypeptides are precipitated in diethylether. Crude product is washed repeatedly with diethylether and then re-precipitated from water-ethanol-diethylether.

Monomer composition is a major determinant of copolymer properties. Copolymer composition depends on the monomer feed composition and reactivity. Reactivity ratios are determined by copolymerization experiments in which the amount of NCA in the initial feed varies vis-à-vis the initiator. After 10-12% conversion of monomers, copolymers are separated by methanol precipitation and dried thoroughly for analysis by $^1H$ NMR spectroscopy and the Finemann-Ross or the Kelen-Tüdös method. A known amount of tryptophan is included in each polymer made for aromatic detection at 280 nm. If tyrosine is present, it too will contribute to absorbance at 280 nm.

Amino Acid Composition Analysis.

Purified polypeptide (c. 0.1 mg) is placed in an ampoule and dissolved in 10 mL of 18 MΩ-cm water. Polymers are hydrolyzed for 24 hours at 110° C. in 200 mL 6 N HCl (with or without 10% phenol) in an ampoule sealed in vacuo, or in the gas phase in the presence of propionic acid or trifluoroacetic acid. The approach depends on amino acid composition; tryptophan and cysteine are partially degraded in strong acid. Tryptophan is important here for quantifying polymer concentration, and cysteine for crosslinking. In some cases, the hydrolysates are dehydrated and redissolved in citrate buffer, pH 3.2, and automated amino acid composition analysis of samples is done on an Agilent 1260 HPLC. In other cases, the resulting monomers are derivatized with 4-N,Ndimethylaminoazobenzene-4'-sulfonyl chloride at 70° C. for detection at the pmol-nmol level in the 420-460 nm range after reversed-phase separation on a C18 bonded silica stationary phase column at ambient temperature. A likely two-eluent mobile phase is 25 mM potassium dihydrogen phosphate (pH 6.8) and acetonitrile:2-propanol (75:25). Internal amino acid standards, for instance, norleucine, are utilized.

Initial Polymer Characterization and Storage.

NMR analysis is done with a Varian 500 or 400 or a Bruker AMX 250 MHz instrument. Deprotected polymer spectra is acquired in $CF_3COOD$ at ambient temperature, and protected polymer and NCA spectra in $CDCl_3$ or DMSO-$d_6$. FTIR spectra for polymer characterization is collected with a Nicolet Magna 550 equipped with attenuated total reflectance and grazing angle accessories. Mass spectra is acquired with an Agilent 6540 LC/QTOF or 6460 LC/QQQ jet-stream electrospray instrument or a Bruker Daltonics AutoFlex MALDI-TOF instrument (800-300,000 Da). Purified polymers are dissolved in LC-MS grade acetonitrile and directly infused into the electrospray instrument in positive ionization mode. The spray voltage is 3-4 kV. The sheath and auxiliary gas pressures is 25 and 15 a.u. The capillary temperatures are 150-270° C. Full spectra is recorded in 0.5 s over a m/z range of 50-200. Product and precursor ion scans are done to verify that observed ions belong to the same molecule. Finally, polymers are dissolved in 3 M NaBr for counterion replacement, dialyzed extensive against ultrapure water, frozen in liquid N2, freeze-dried and stored at −20° C. prior to materials fabrication.

Polymer Size Analysis.

Polymers are separated by gel permeation chromatography to assess average molar mass M, mass distribution function p(M) and polydispersity index $\chi$. $\int p(M)dM=1$, where the integration limits are 0 and co. The column is calibrated with several proteins and monodisperse ELPs in 6.00 M guanidine hydrochloride (GuHCl) instead of polystyrene standards in water to account for the possible influence of backbone hydrogen bonding on measured values. Concentrated GuHCl ensures protein denaturation and a short Debye length. It is expected that $\log(M[\eta s])$ and $\log(n[\eta s])$ are linear functions of elution volume, where n is number average DP and $\eta s$ viscosity of solution (Nicholson, 2006). $\chi=[(1/m)\Sigma m_i M_i]/[(1/N)\Sigma N_i M_i]$, where mi is total mass of molecules of molar mass Mi, m total mass of the sample, Ni number of molecules with molar mass Mi and N total number of molecules. For typical polymers, $\chi \approx 4$. If chain length is Poisson distributed, as expected, then $\chi-1=1/n$ (Strobl, 2007). $\chi$ can be decreased by fractionation. Measurements are made at 25° C. Samples are analyzed on a Shimadzu size-exclusion chromatograph, consisting of two 10 ADvp pumps, a system controller, a dual wavelength UV-vis detector, a refractive index detector and a Waters HR 4E styragel column.

Polymer Solution Analysis.

Solution viscosity and the number average molecular mass of polymers are determined as follows. Flow time for polymer at a given concentration (g/100 mL) and relative solution density (ratio of solution density to that of the solvent, $\rho s/\rho 0$) is measured with an Ostwald viscometer. Polymer concentration, C, is measured independently by mass of lyophilized polymer and absorbance at 280 nm, accounting for the extinction coefficient aromatic side chains in 6.00 M GuHCl (Gill and von Hippel, 1989) and the mole fractions of these amino acids in the polymers. At least four concentrations are analyzed for each polymer. The intrinsic viscosity $[\eta]$ is determined as follows. For laminar flow, from Poiseuille's law the ratio of the viscosity of solution ($\eta s$) to the viscosity of pure solvent ($\eta 0$) is the relative viscosity $\eta_r=\eta_s/\eta_0=t_s\rho_s/t_0\rho_0$. The solvent is 6.00 M GuHCl. Solution density is determined as the mass of a fixed volume of solution, 1000 μL. The specific viscosity $\eta_{sp}=\eta_r-1$. $[\eta]$ is determined in units of mL/g from $\eta_{sp}/C$ as $C \to 0$. In this limit, $[\eta]=v\bar{v}$, where v depends on solute shape (2.50 for a sphere) and $\bar{v}$ is the specific volume of the solute. $[\eta]=vN_A v_m/M$, where $N_A$ is Avogadro's number, vm is molecular volume and M is molecular mass. If $v_m=K'''R_G^3$, where $R_G^3$ is radius of gyration, then $[\eta]=K'R_G^3/M$; K" and K' are constants. Concentrated GuHCl is better than a 0 solvent for polypeptides, so $[\eta]=K'M^a$; K and a are Mark-Houwink parameters and $a > \frac{1}{2}$ (Tanford, 1961). K and a are usually independent of M, the viscosity-average molecular mass, but they vary with polymer, solvent, temperature and mass distribution. A modified form of the Mark-Houwink equation, $[\eta]=Kn^a$, where n is the viscosity-average DP, is used. Begin with the assumption that $K=0.716 \times 10^{-2}$ and $a=0.66$, as for various proteins dissolved in 6.00 M GuHCl at 25° C. (Tanford et al., 1967), but the parameters for the present polymers may be adjusted as appropriate to determine n by measurement of $[\eta]$. All viscosity measurements are made at 25° C.

Polymer Size Analysis by Light Scattering.

By the Stokes-Einstein equation, $r=kT/6\pi\eta_s D$, where r is the weight-average hydrodynamic radius of the polymers, k the Boltzmann constant, T the absolute temperature and D the diffusion constant. Note that r is the equivalent hydrated sphere radius. The average polymer conformation depends on solvent composition, and changes in conformation affect the diffusion rate. DLS is very sensitive to such changes. For each polymer, r is measured at 25° C. as a function of C and [GuHCl]. $\eta s$ is obtained as above. The data provides insight on polymer association and therefore chain entanglement in the materials fabrication feedstock. All polymer solutions are filtered at 0.22 μm prior to measurement, eliminating particulates. Data is acquired at 633 nm with a Malvern Instruments Zetasizer NanoS. The scattering angle is 173° to reduce multiple scattering and enable analysis of concentrated samples. Instrument performance is verified with a polystyrene latex standard in 10 mM NaCl to suppress the electrical double layer.

Polymer Multimerization Analysis.

Polymer association decreases transmitted intensity at a scattering angle of 0° as $I_t=I_0\exp(-\tau cl)$, where $\tau$ resembles the extinction coefficient in the Beer-Lambert law. $\lambda=330$ nm as in Wetlaufer and Xie (1995) is used. Sensitivity is high at this wavelength, because scattered intensity $\lambda^{-4}$ but aromatic absorption is negligible. Polymers are dissolved in 5.00 M GuHCl and diluted rapidly to 1.00 M with buffer (e.g. 50 mM Tris-sulfate, pH 7.4). Turbidity is measured as apparent absorbance in a 1.0-cm path length quartz cell after 10 s and then at frequent intervals after mixing. There are 3 replicates at minimum. Turbidity is likely to plateau after about 100 min. All measurements are made at 25° C. The data provides insight on chain entanglement.

Polymer Conformation Analysis by CD.

Polypeptides are chiral polymers; they absorb left- and right-circularly polarized light to different extents in the UV. It is often possible to obtain a good sense of the secondary structure of a peptide from its far-UV CD signature. CD analysis of the structure of a random co-polypeptide in aqueous solution appears in a recent study (Haynie et al., 2012). CD can be utilized to monitor changes in structure, for example, by changing [GuHCl] up to 6.00 M, and thus determine the thermostability of structures in solution. Here, mean molar ellipticity per residue [θ] is measured v. wavelength from 190 nm to 260 nm. Differential absorption, $\Delta A$, is converted to $[\theta]=3300\Delta A/nCL$, where n is the average DP and L is the path length. GuHCl is used in attempts to dissociate oligomers and unfold individual chains. Thermostability in the absence of GuHCl is determined by assuming that stability depends on GuHCl as $\Delta G=\Delta G°-m[GuHCl]$, where ΔG° is the stability of the average conformation relative to a fully solvated polymer under standard conditions (here, pH 7.0 and 25° C.) and the fitting parameter m is roughly the average surface area of polymer not exposed to solvent in the absence of denaturant [e.g. Haynie and Freire (1994) and references cited therein]. All measurements are made at 25° C. The data provides information on polymer association in solution and insight on chain entanglement in the feedstock.

Materials Fabrication.

The chains are flexible; the contour length will be much greater than the persistence length. Materials are fabricated from semi-dilute aqueous solutions, not polymer melts. The polymer concentration is c. 50% (w/v) for electrospinning and possibly lower by a factor of 2-5 for other approaches to fabrication. Polymers are generally entangled in solution, and the viscoelastic relaxation time long. Concentrated solutions look like an elastic solid on a short time scale and a viscous fluid on a long time scale. Fibers are made by electrospinning as in previous work (see FIGS. 4-8). In most cases, the spinneret potential is c. 10 kV and the collector distance c. 10 cm. The inner diameter of the die is c. 0.5 mm. Flow rate regulation is optional. Fiber alignment details are provided elsewhere in the Materials and Methods. Molded materials are prepared as in FIG. 9 and discussed elsewhere in the Materials and Methods.

Birefringence Analysis.

The materials of this study are amorphous solids. Polymers tend to be in a random coil conformation in a polymer melt by the Flory theorem. Fiber geometry is determined largely by the spinneret. There is a net orientation of molecules on the fiber surface, but because the surface area is much larger than the size of a single polymer, the surface is like a plane to a polymer, and any portion of the polymer on the surface is randomly oriented. No strong anisotropy is expected in binding forces, even in fibers. Valence forces are in all directions, except at fiber surface, and the same for van der Waals forces. Materials are nevertheless analyzed for possible polymer orientation, as the directional correlation of molecules could influence mechanical properties. Samples are illuminated with polarized light. If the interaction with light is non-uniform across a sample, the polymers are oriented. Contrast enhancement of the image can reveal details of the structure of the sample. Any phase difference between the fast and slow directions of polarized light passing through the sample will vary with wavelength and thickness. Optical path difference=$(\Delta n)t$, where t is thickness. The phase difference between two perpendicular polarizations is $\delta=2\pi[(\Delta n)t/\lambda]$.

Elemental Composition Analysis by X-Ray Spectroscopy.

The composition of peptide-based materials is analyzed with an INCA X-sight 7582M energy-dispersive spectrometer (Oxford Instruments) mounted on a JSM-6390LV scanning electron microscope (SEM; JEOL). At least 5 mg of material is deposited on a suitable substrate. The potential is 15 kV. The calibration standard is Cu tape. Raw data may be normalized for the integrated intensity of a species of atom. We have previously shown that PLEY fibers contain a large quantity of $Na^+$ and PLO fibers a large quantity of Br (Haynie et al., 2012) and an increase in pH or solvent annealing in water elicits the release of $Na^+$ from fibers (Haynie et al., 2013; unpublished data).

Polymer Conformation Analysis by FTIR.

Polypeptide conformation in solution, cast films and fibers are analyzed with a Jasco FT/IR 4100 spectrometer outfitted with a Horizon™ multiple-reflection attenuated total reflection accessory with a ZnSe crystal (Harrick Scientific Products, Inc.), as in Khadka et al. (2011) and Haynie et al. (2012). The transparency of ZnSe is approximately independent of wavelength in the 1200-4000 $cm^{-1}$ range. Solution samples and anhydrous samples are placed directly on the ZnSe crystal. Spectra is acquired as 256 scan averages at 4 $cm^{-1}$ resolution. For solution samples, the polymers are dissolved in D2O. It should be noted that it is important to know the kinds of structure formed in materials, as it can influence the mechanisms of elasticity, the elastic modulus and resilience.

Polymer Crosslinking.

All polymer crosslinking is done ex post facto and in situ. Reactions are controlled in two ways: polymer design and thereby the general crosslinking method, and process parameters. Some elastic moduli of the material is non-vanishing even after crosslinking 25%-75% GTA is used to crosslink peptide materials containing free amino groups in the vapor phase (Khadka and Haynie, 2010). 50 mM EDC in 95% ethanol is used to crosslink peptide materials containing free carboxyl groups and free amino groups on submersion in ethanol. PLEY is soluble in water but not ethanol (Khadka et al., 2011; Haynie et al., 2013). For disulfide crosslinking, the materials are exposed to air or oxygen-saturated water or aqueous buffer.

Crosslinking Analysis.

A published protocol is incorporated herein by reference (Haynie et al., 2013). A similar approach is taken for the novel polymers of this invention. 2,4,6-trinitrobenzene sulfonic acid (TNBSA) reacts with free amino groups. Polymer samples are incubated in an aqueous solution of TNBSA at pH 8.5, and the formation of reaction product is quantified as the absorbance of the soluble fraction in the 335-355 nm range. A c. 2 mg sample on a transparent substrate, cross-linked overnight with EDC dissolved in 10 mL ethanol at a final concentration in the 0-200 mM range, is gently rinsed next day with DI water for 2 minutes, incubated in DI water for 1 hour to ensure hydrolysis of residual O-acylosourea intermediates, rinsed again with deionized water and dried in a dessicator for at least 2 hours. Cross-linked material is then desorbed from the substrate with 4% $NaHCO_3$ solution and mechanical agitation. Samples are inspected by light microscopy to ensure that treatment has removed all solid material. Material thus collected is maintained in separate glass tubes, one per sample. 4% $NaHCO_3$ solution is added to a final volume of 1.5 mL per tube to control the pH of the dye conjugation reaction. A 1.0 mL aliquot of 0.01% TNBSA in 4% NaHCO3 solution is then added to each tube. This results in a 6:1 mole ratio of dye to polymer chains, assuming a polymer mass of 32 kDa. Samples are sealed with screw caps, wrapped tightly with parafilm and heated at 40° C. for 2 hours to promote the reaction of TNBSA with free amino groups. Next, 3 mL of 6 N HCl is added to each sample. Samples are sealed with screw caps, wrapped tightly and heated at 60° C. for 2 hours to hydrolyze the PLEY molecules into oligopeptides. After 30 minutes of cooling, the pH of each sample is measured. Samples are inspected by light microscopy to ensure that no fibers remain. The absorbance of each sample is then measured at 345 nm, where there is a large peak in the TNBSA spectrum. The efficiency of dye labeling is determined by dissolving a nominal mass of 2 mg of lyophilized polymer (~$10^{17}$ molecules, depending on the molar mass of the chains) in 1.5 mL 4% $NaHCO_3$ solution, measuring the absorbance of the resulting solution at 274 nm and following the remaining steps of the procedure outlined above. The mole ratio of dye to polymer chains under these conditions is 6:1, assuming a polymer mass of 32 kDa. The percentage of sites crosslinked are calculated as $1-(A_c/m_c)/(A_{nc}/m_{nc})$, where A is the measured absorbance and m is measured mass of the fiber sample, and the subscripts represent samples that were cross-linked or not cross-linked.

Hydration Analysis.

A published protocol is incorporated herein by reference (Haynie et al., 2013). A similar approach is taken for the novel polymers of this invention. The amount of water in 2.0-mg samples is estimated as follows. Non-cross-linked samples are dissolved in water, the absorbance read at 274 nm, and the number of moles of aromatic side chains calculated from the extinction coefficient for the polymer (e.g. $1400 \times 10^3$ cm$^2$ mol$^{-1}$ for tyrosine) and the Beer-Lambert law. The result is divided by the average number of aromatic residues per polymer chain to find the amount per polymer. The result is multiplied by the average molecular weight of the polymer. The result is subtracted from 2.0 mg. The amount of water thus determined should be <25%.

Surface morphology analysis.

A JEOL JSM-6390LV SEM is utilized for fiber and film morphology analysis after metalizing with 10 nm of gold. The accelerating potential is in the 10-30 kV range. For molded materials, sample preparation proceeds as follows. Dehydrated or partially hydrated samples are soaked in successive ethanol baths in 50 mL tubes: 1) 35% for 15 minutes, 2) 70% for 15 minutes, 3) 95% for 15 minutes, 4) 100% for 5 minutes, 5) 100% for 5 minutes and 6) 100% for 5 minutes. Swelling of the sample may occur in the process. Samples in the final ethanol bath are sealed inside the tubes, which is then placed in a critical point dryer at 20° C. The dryer is half-filled with liquid $CO_2$ and, after 15 minutes, ethanol and much of the $CO_2$ is drained out. This process is repeated twice. After refilling the chamber with $CO_2$ again, the temperature is increased to 45° C., exceeding the critical point of $CO_2$. This enables liquid $CO_2$ to become gas in the absence of a phase change; there will be no change in the surface tension acting on the solid material as the liquid disappears. Samples thus prepared are sputter-coated with gold for SEM analysis. AFM enables measurement of the topography of surfaces at the nanoscale. Surface images of dehydrated multilayer films are obtained in air with a Q-Scope 250 AFM (Digital Instruments, USA) operated in tapping mode. Cantilever tips of resonant frequency 300 kHz, force constant 40 N/m and tip radius <10 nm is utilized.

Mechanical Testing of Fibrous Materials.

Figure 13:
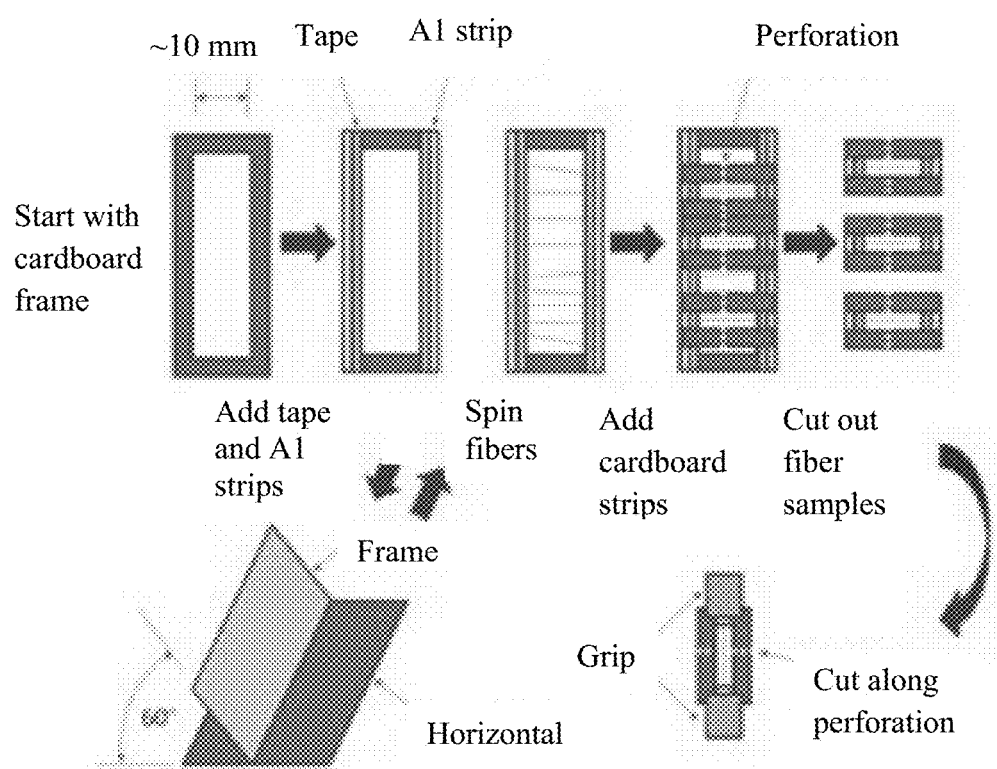
FIG. 13 shows sample preparation for single-fiber analysis. Fibers are spun onto a cardboard frame for attachment to a universal testing machine. Red arrows indicate the flow of the process. Finally, the sample frame is oriented for analysis and held in place by grips attached to the universal testing machine, and the vertical sides of the frame are cut along the perforations, making a single fiber the sole mechanical contact between grips. It is assumed that hydration will be relevant to measured values.
Figure 14:
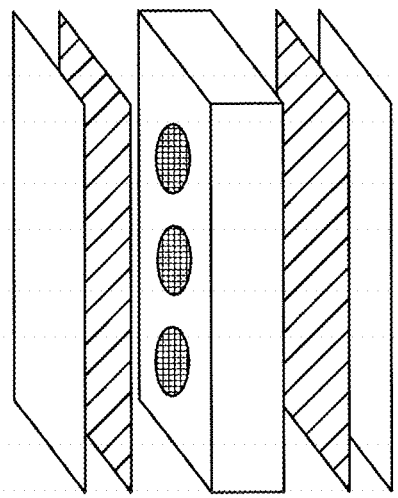
FIG. 14 shows a molded sample for compression testing. Cylinders, 4 mm in diameter, were cut into a block of aluminum 4 mm thick to prepare molded samples. A schematic cylinder is shown in green. The photograph to the right shows an actual sample viewed from above. The photograph to the left shows the cylinders cut into the aluminum block. The schematic at the far right depicts the aluminum block for sample preparation, two gaskets (orange), and two plates, one for each side of the block.
Figure 14:
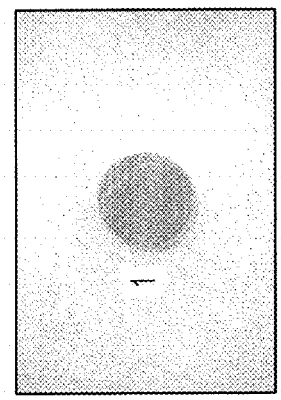
Figure 14:
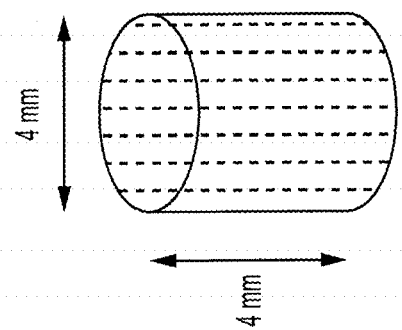
Figure 14:
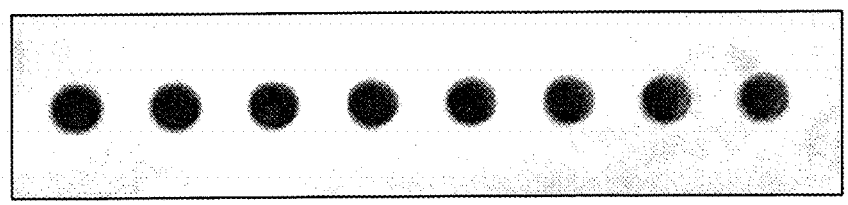
Figure 15:
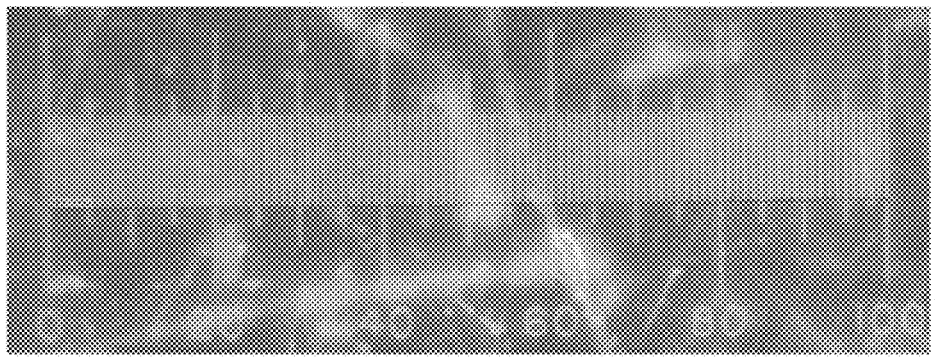
FIG. 15 shows a 5 mm reticule for photographic quantification of size of molded cylindrical samples.
Figure 16:
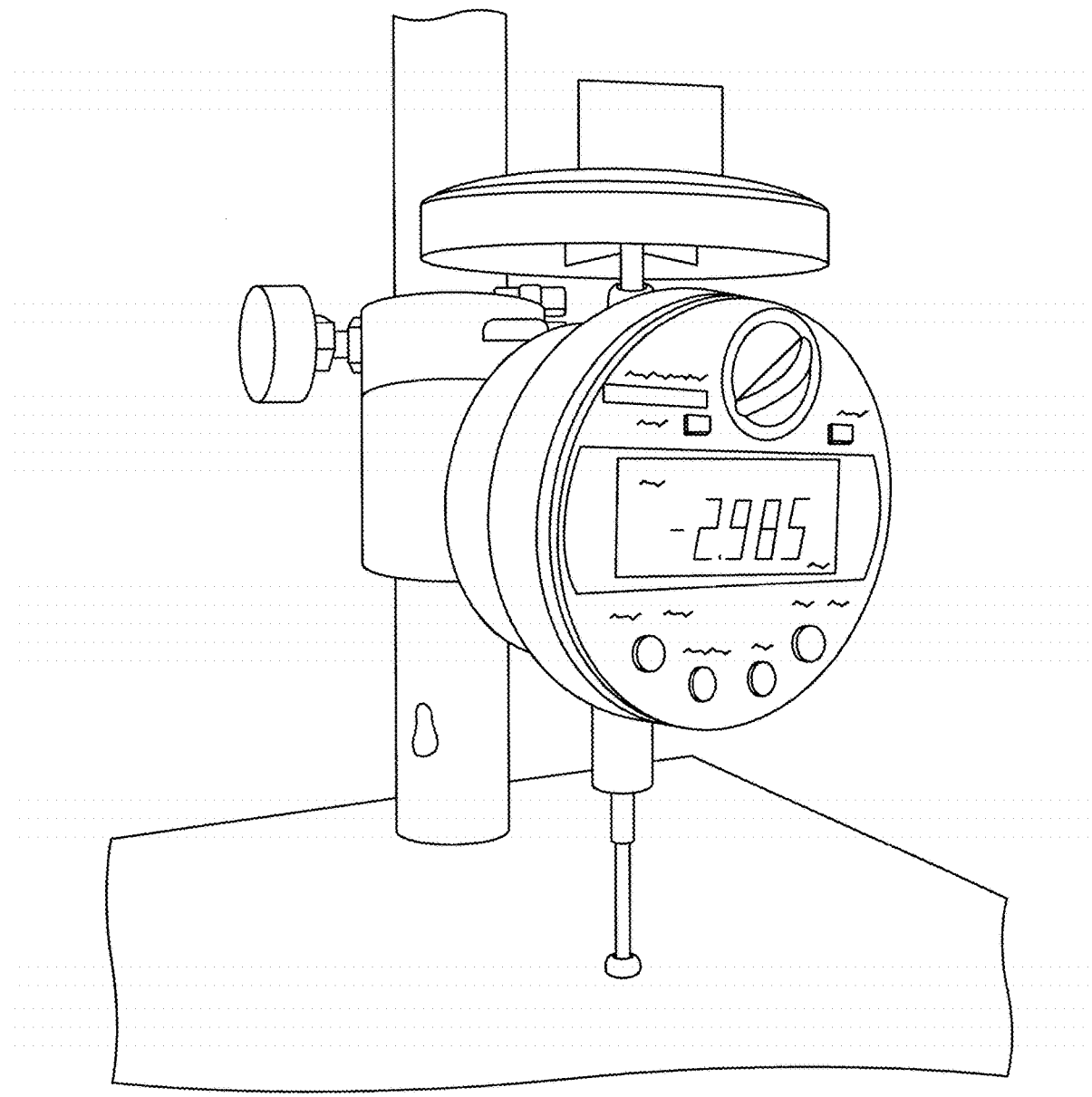
FIG. 16 shows a displacement gauge for compression testing. The apparatus can be used to measure the deformation of a sample, for example, a cylinder, under an applied stress, or force per unit area.
Figure 17:
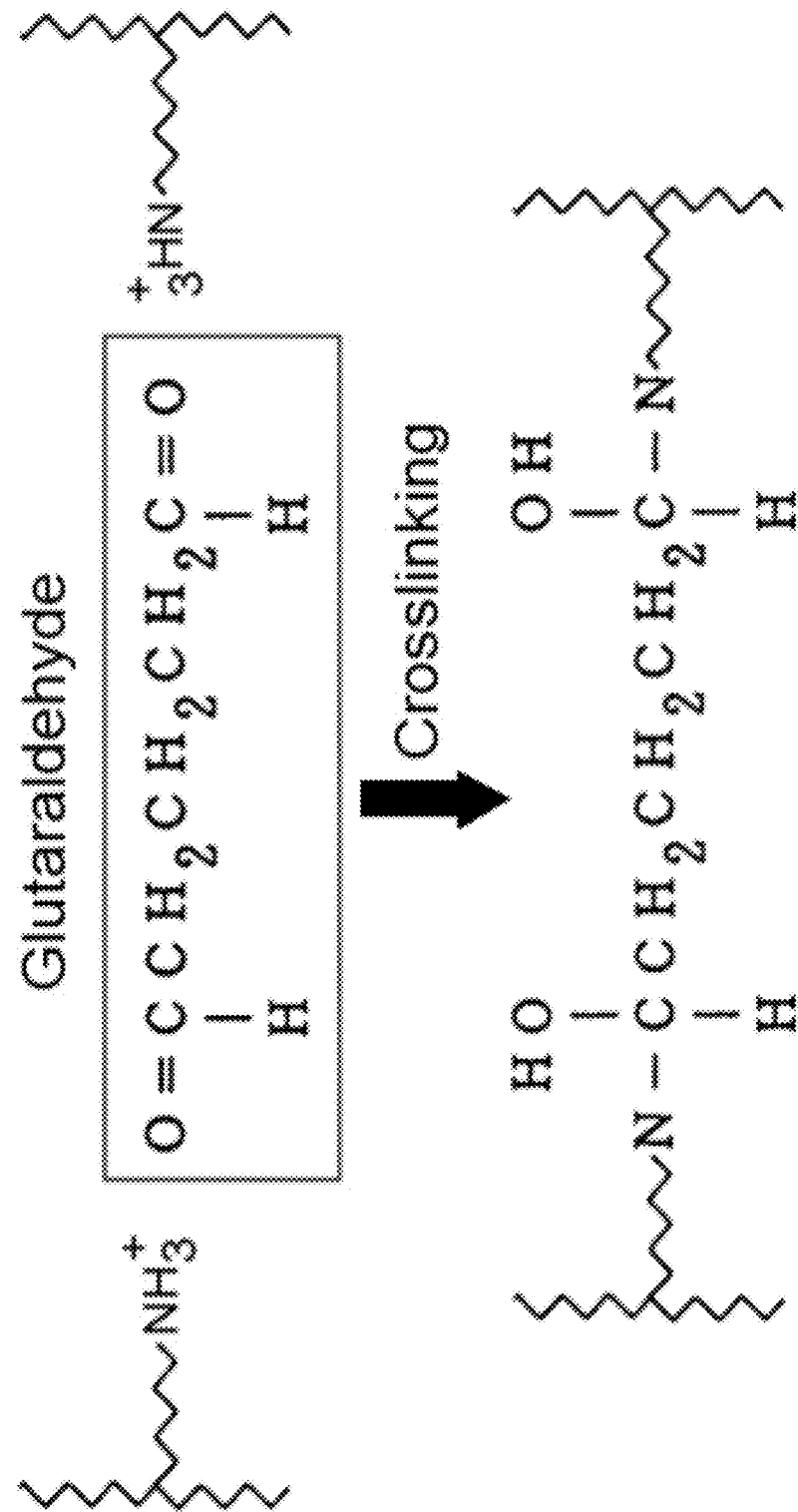
FIG. 17 shows a crosslinking reaction of an embodiment of the present invention. Specifically, glutaraldehyde, a symmetrical bifunctional reagent, is depicted forming a crosslink between two amino groups, for example, the epsilon amino group of a lysine residue in a first polymer chain and the epsilon amino group of a lysine residue in a second polymer chain.
Figure 18:
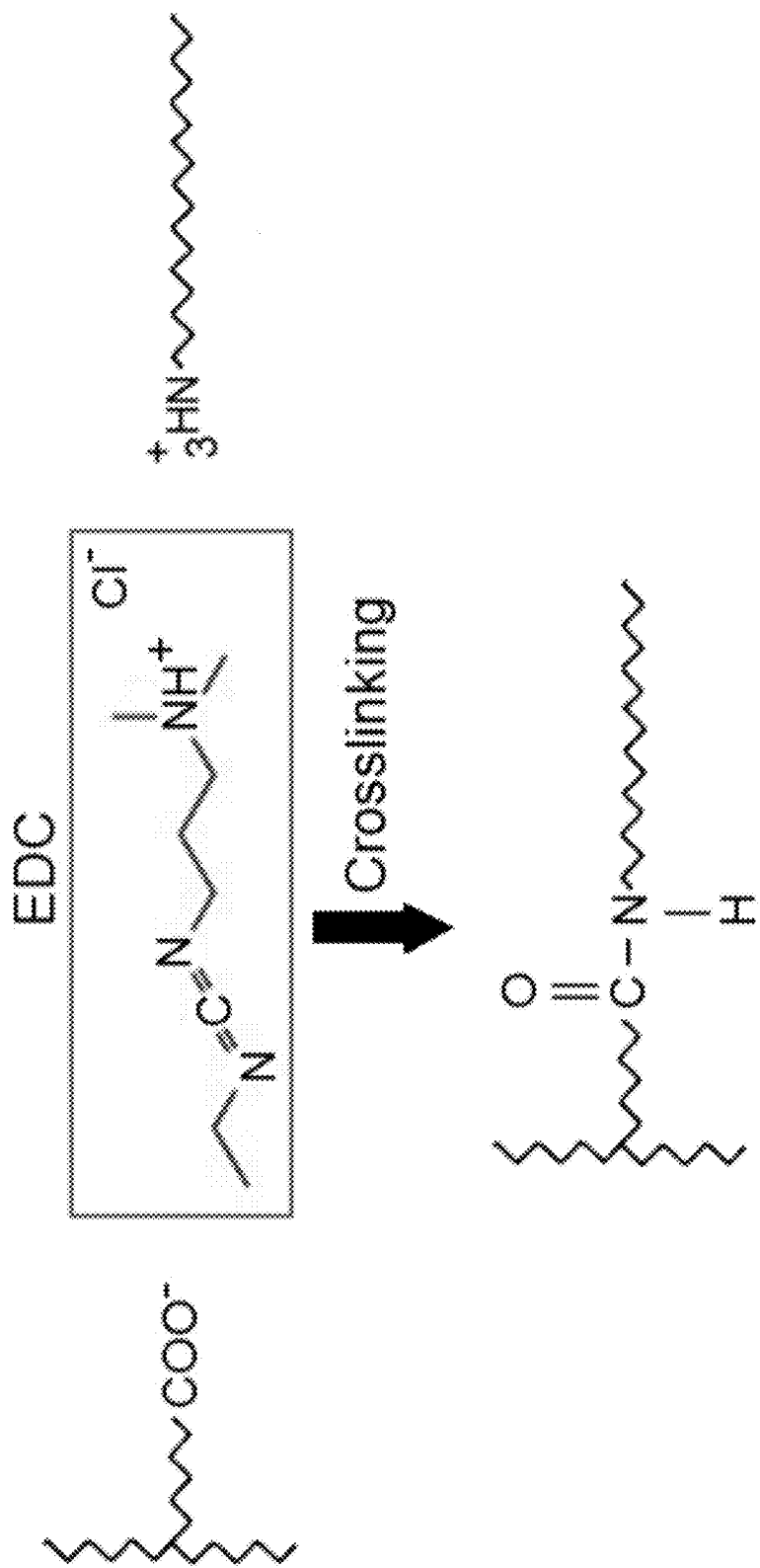
FIG. 18 shows a crosslinking reaction of an embodiment of the present invention. Specifically, EDC, a diimide reagent, is depicted forming a "zero-length" crosslink, a peptide bond, between a carboxylate group, for example, the delta carboxylate group of a glutamate residue in a first polymer chain, and an amino group, for example, the epsilon amino group of a lysine residue in a second polymer chain.
Figure 19:
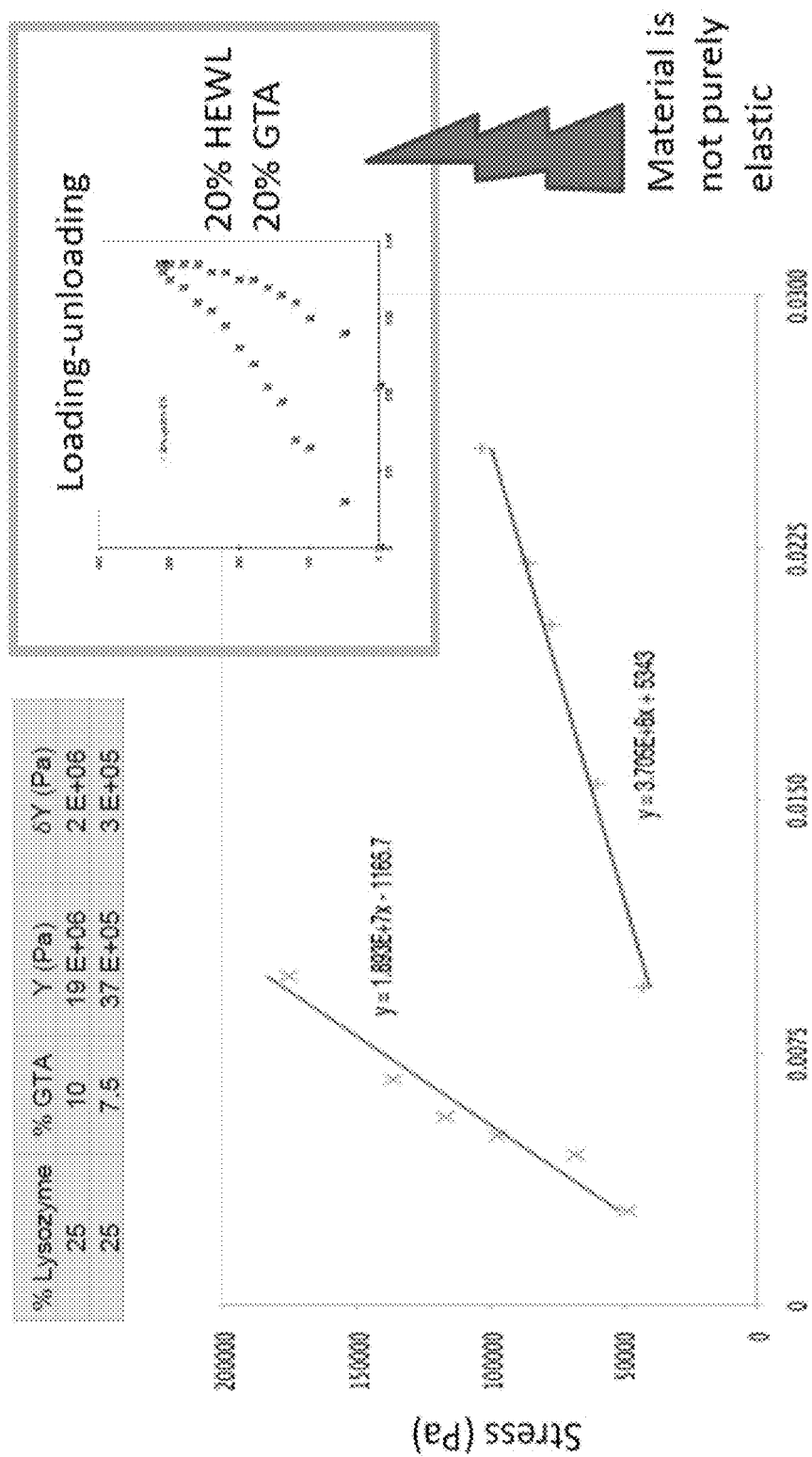
FIG. 19 shows Young's modulus determination. Cylindrical samples, prepared in an aluminum mold at a specified concentration of protein and crosslinking reagent, were chemically dehydrated and then subjected to compression at a known force per unit area, or stress. The change in height of the sample was measured with a displacement gauge for known values of applied stress. Stress was then plotted versus strain, or fractional change in size of the cylinder, giving a stress-strain curve. The initial slope of the resulting curve is known as Young's modulus, or the elastic modulus, of the material tested. The inset provides evidence of hysteresis in a sample; that is, a lack of coincidence in the loading and unloading curves in a test to determine Young's modulus.
Figure 20:
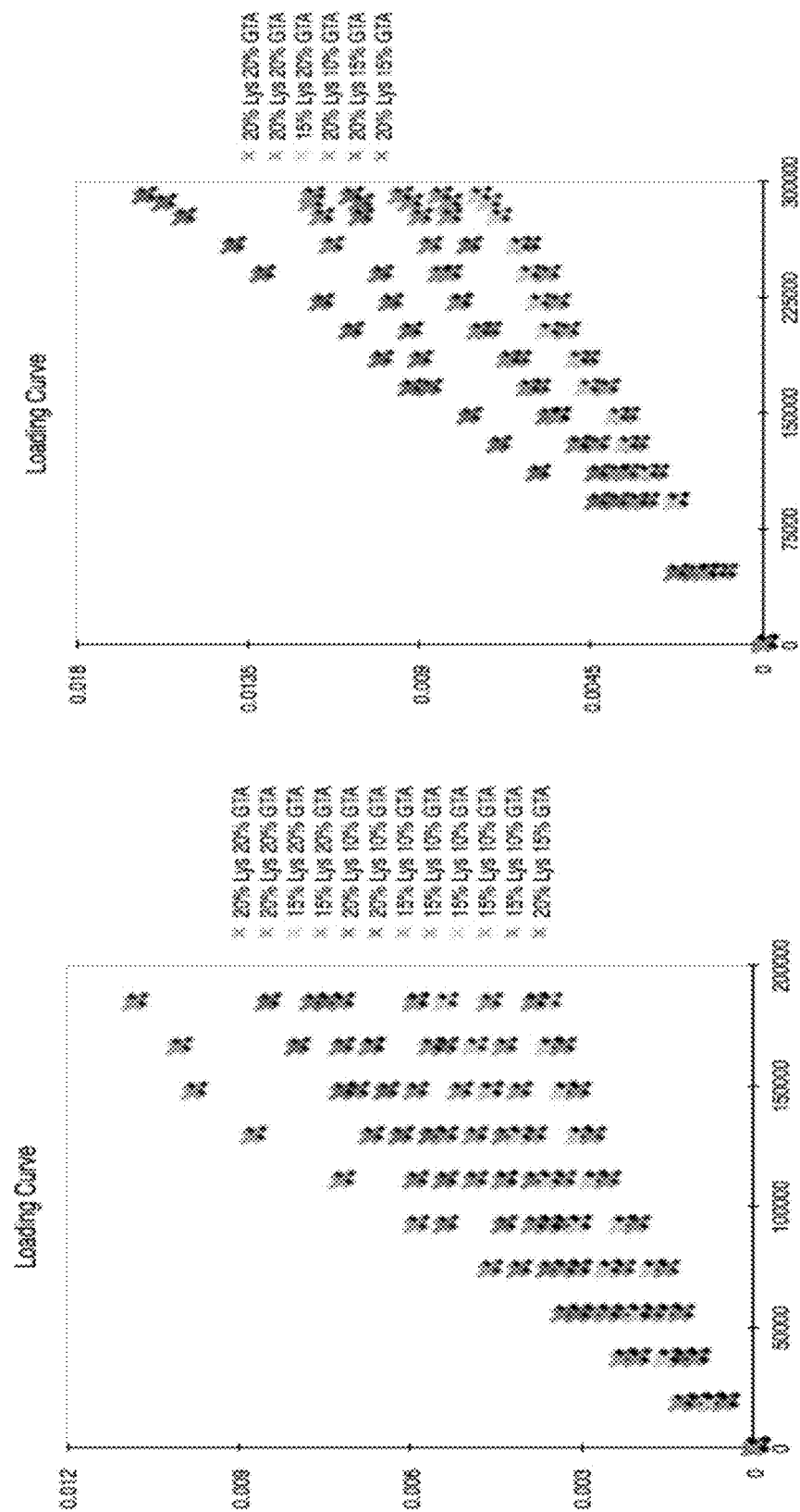
FIG. 20 shows Young's modulus determination of a series of samples of identical or similar composition.
Figure 21:
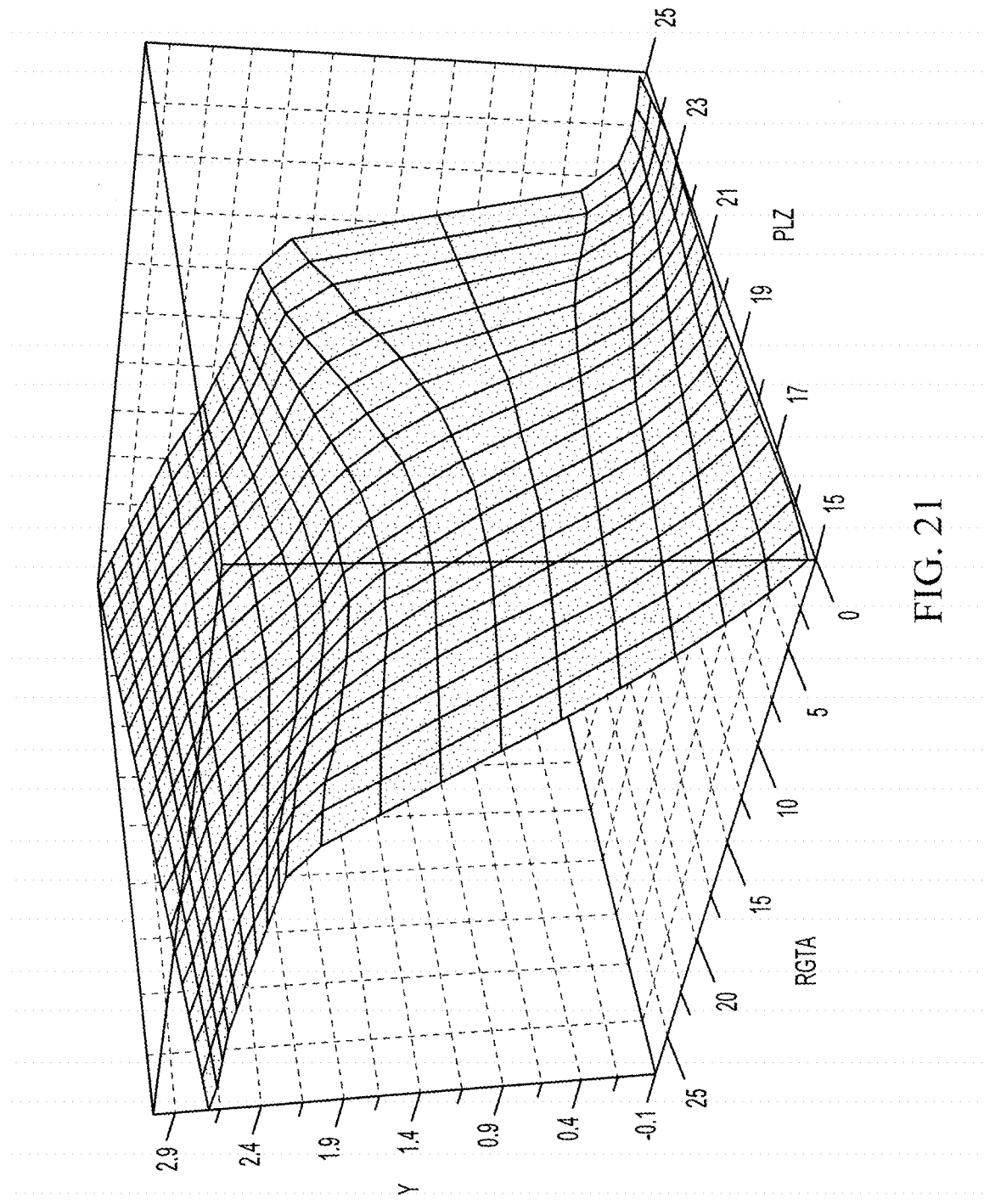
FIG. 21 shows the stiffness-GTA-LZ relationship. The test specimens were 4 mm×4 mm cylinders of crosslinked protein. Lysozyme concentration was 15-25% (w/v). GTA concentration, which was 10-20% (w/v), is presented as the molar ratio of GTA to protein amino groups. There are 7 amino groups per lysozyme molecule (6 side-chains+1 N-terminal a). Native lysozyme has four disulfide bonds. The molecular mass of the protein is 14.3 kDa. In general, Young's modulus will be a function of polymer concentration (here, lysozyme), crosslinker concentration (here, GTA), reaction time and hydration. Crosslinking reactions were carried out overnight, and samples underwent extensive chemical dehydration prior to analysis.

The mechanical analysis of single fibers provides insight on the physical properties of nanofibrous scaffolds. What follows is modified from Tan et al. (2005). Aligned fibers are spun across two conductive strips in parallel (Li et al., 2003; Khadka et al., 2011). All strips are affixed to a cardboard frame with a 10-mm gap (gage length) for electrospinning See FIG. 13. Double-sided tape is attached to the frame for fiber adhesion. The frame is oriented at a 60° angle relative to horizontal for fiber spinning Well-aligned single fibers are identified by microscopy (a dissecting microscope is sufficient). Strips of cardboard are glued to the frame on each side of these fibers. The framed fibers are then cut from the larger frame. Horizontal edges enable sample gripping. Vertical edges are cut along the perforations for single-fiber analysis (FIG. 13). A Nano Bionix System (MTS) is needed for the purpose. The instrument has a maximum load rating of 51 g, and it is suitable for both quasi-static and dynamic analysis of viscoelastic materials. Portions of fiber adhered to tape are assumed to be immobile. Samples are stretched to failure at a constant strain rate of 0.5-2%/s at ambient temperature (22° C.). Yielding may occur prior to fracture. Fiber material on the corresponding part of the larger frame is sputter-coated with gold for analysis by SEM. Fiber diameter is determined by analysis of SEM micrographs with ImageJ (NIH freeware). If a ribbon-like fiber morphology is obtained, width and thickness is measured, with accuracy on the order of a few nm/µm.

Data obtained by Tan et al. (2005) for poly(caprolactone) fibers spun at ambient temperature were 120±30 MPa for tensile modulus, 40±10 MPa for tensile strength, 200±100% for strain at break, 13±7 MPa for yield stress, 20±10% for yield strain and 1.4±0.3 µm for fiber diameter (by light microscopy). The glass transition temperature of poly (caprolactone) is well below 300 K. Other useful comparables are for the elastomeric insect protein resilin. Vincent and Wegst (2004) found that Young's modulus Y=0.3-3.0 MPa. For comparison, Y 200 GPa for steel, 80 GPa for dry cellulose and ~1 GPa for plastics and collagen (Shen et al., 2008). For polypropylene, Teflon, polyisoprene, silk (*Bombyx mori*), keratin (hair) and elastin, Y=2.4, 0.34, 0.02, 5-10, 2.4 and 0.002, respectively, all in GPa (Howard, 2001). Most protein filaments have Y≈1 GPa (Boal, 2012). Wetness will influence stiffness, as is evident from measured values for intermediate filaments from hagfish slime: Y falls 600-fold, from 3.6 MPa to 0.006 MPa, when hydrated (Fudge and Gosline, 2004). Flexural rigidity for a strand of human hair, which comprises a number of different proteins, is $K_{eff}=YI \approx 5 \times 10^{-9}$ J-m (Boal, 2012), where I=πR4/4 is moment of inertia of the cross section of solid cylinder and R is radius of curvature. As to tensile strength, for polypropylene, Teflon, polyisoprene, silk (*Bombyx mori*), keratin and elastin, the values are 35, 22, 17, 300-600, 200 and 2, all in MPa (Howard, 2001). It is anticipated that glass transition temperatures of the materials of this invention are <300 K in some cases and >300 K in others, after dehydration, depending on enthalpic interactions. Further, as fiber diameter increases, tensile strength and yield stress and strain will decrease but strain at break will increase, but Young's modulus is roughly independent of diameter. Single fibers are dehydrated in a dessicator and hydrated by soaking in an aqueous solution for at least 4 hours. Excess water is removed from the fiber by blotting with absorbent paper. The statistical significance of all correlations is quantified as outlined below.

Single fiber analysis is more advantageous than study of nanofibrous scaffolds for extrapolating measurements to the single-molecule level. Accurate values of fiber diameter and polymer density in fibers are needed. Polymer density is measured as follows: Parallel electrodes are used to collect a small number of oriented fibers on a piece of ITO-PET (Khadka et al., 2011). Two adjacent regions of known area are excised from a larger fiber-coated substrate and dehydrated overnight. The fibers on one of two pieces are sputter-coated for analysis by SEM. Average fiber diameter and average number of fibers per unit area of substrate is determined. The fibers on the other piece are dissolved in a known volume of water. Absorbance of the resulting solution is measured at 280 nm. The known amino acid composition of the polymers and extinction coefficients of aromatic side chains permit determination of the mass of polypeptide in the fibers by the Beer-Lambert law to within ~5%. The volume occupied by fibers is found by assuming perfectly cylindrical geometry.

Polymer density in fibers is then calculated as the ratio of polymer mass in fibers to fiber volume. The density thus obtained is compared with accepted values for proteins. A typical value is 1.4 g/cc.

An alternative approach to force analysis now follows: The ends of a single fiber are glued with a silicone adhesive (e.g. Dow Corning 3140/3145 RTV, 1:1 mixture) to glass microneedles, one connected to a piezoelectric motor and the other to a force transducer. Force data is collected and the motor controlled with a data acquisition board (e.g. National Instruments PCI-MIO-16-E1) and software (e.g. Lab-VIEW). Light micrographs of fibers under stretch are simultaneously recorded with a CCD and frame grabber. The needles are marked to quantify the separation distance at ~0.5 μm resolution. Fibers are stretched for a duration of ~10 seconds. The hold period is 1-2 min. After maximum stretching, specimens are released. Force data is recorded every 4 ms throughout the process. Fiber cross-sectional area is determined by SEM. In some experiments, a small-amplitude sinusoidal oscillation is imposed on the stretched fiber. The fiber either is or is not hydrated, and the buffer surrounding a hydrated sample either does or does not contain NaCl, and the concentration of NaCl will be known, as for instance in the analysis of titin in sarcomeres of Linke et al. (1998).

Modeling of Fibrous Materials.

The fibers of this invention are mesoscopic aggregates of chains, not individual chains. Therefore, neither the random-flight nor the worm-like chain is used to interpret experimental data. Entropy dominates the elastic behavior of the soft, dehydrated materials, whereas for stiff materials, deformation is dominated by energetic interactions. Stiffness varies with crosslink density and thus molecular design and hydration. The linear density (mass per unit length) and crosslink density of materials is determined. Measured mechanical properties for the number of chains per unit volume or crosssectional area are normalized. The resulting values are suitable for comparison with the results of corresponding single-molecule experiments.

The elastic energy of dehydrated fibers under tension or compression can be modeled as $E=YA\Delta L^2/2L_0$, where Y is Young's modulus, A is the cross-sectional area of a cylindrical, $L_0$ is the original length of the sample, $\Delta L$ is the change in length under stretch and the spring constant $k=YA/L_0$, as for a perfectly elastic spring. The materials of this invention are usually not perfectly elastic. The applied force $F=k\Delta L$ is measured; k is determined by measuring $\Delta L$. Y is readily calculated from k, A and L0. A, $\Delta L$ and $L_0$ is obtained by SEM or the Nano Bionix System instrument noted above, or alternatively by analysis of micrographs obtained with a CCD. The bending energy is measured as $E=YIL_0/2R^2$, the buckling force as $F_b=\pi^2 K_{eff}/L_0^2$ and the persistence length as $\xi=\pi YR^4/4k_BT$.

Mechanical Testing of Macroscopic Materials.

Physical properties must be measured to assess the suitability of a material for a process or end-use application. Physical properties are determined. Solid samples are molded in aluminum blocks as rectangular bars 5 mm square and 5 mm or 15 mm long, or as dumbbells 50 mm long, 4 mm inner width, 25 mm gage length and 2 mm thick (see DIN-53504 S3). Samples are swelled in aqueous solution to different levels of water content, from the water content calculated from the reactant ratio to the required content, and then kept in sealed plastic bags for 7 days to ensure uniform swelling. Immediately prior to analysis, samples are coated with a thin layer of silicone oil to limit water evaporation. At least three specimens are tested of each polymer and water content.

The Nano Bionix System instrument mentioned above is also used for macroscopic materials characterization. The tensile strength and Young's modulus of bars is measured by obtaining stress-strain curves for the dumbbell-shaped samples. The extension rate is 1-10 mm/minutes and constant up to a set strain or stress. Cyclic tensile tests are done after initial loading at a crosshead speed of <800%/min. Hysteresis in the loading/unloading curves is expected. Tensile stress relaxation tests are done by stretching a specimen to a fixed strain, maintaining the strain for a first 5 minutes at ambient temperature, and testing the same specimen at an increased strain level for second 5 minutes. Uniaxial compression tests are done on cylindrical specimens at a crosshead rate of 1-10 mm/minute. The flexural strength and modulus of samples is assessed by three-point bending of cylindrical specimens at a rate of 1-10 mm/minute. Resilience depends on the rate of stretch and the energy of deformation. The rebound resilience of molded materials, that is, the ability of the materials to deform and recover, is measured with a Shore type SRI resilometer (applied for here). Resilience is quantified as the percentage height to which the top of a 28-g plunger rebounds. 6 tests are averaged. Resilin has a measured resilience greater than that of polybutadiene, the polymer used to make Super Balls (Elvin et al., 2005), >90%.

Modeling of Macroscopic Materials.

Stress is linearly proportional to strain as an elastic material. Tensile stress is calculated as $\sigma_t=F/tw$, where F is the load, t is the initial thickness and w is the inner width of the sample. Tensile strain is defined as $\epsilon_t=(L-L_0)/L_0$, the change in length divided by the original length of the sample. Tensile fracture stress $\sigma_t$, and tensile fracture strain $\epsilon_1$, is assessed at fracture. Initial tensile modulus Y is determined as stress/strain in the linear part of the curve (low strain, 10-30%). Hysteresis is quantified as $hr=\Delta S/S$, where $\Delta S$ is the area of the loop and S is the integrated area of the loading curve.

The example outlined above yields flexural stress $\sigma_f=3PL/2bd^2$, where P is the load in N, L is the support span in mm, and b and d are the width and depth of the rectangular beam in mm; flexural strain $\epsilon_f=6Dd/L^2$, where D is the maximum deflection of the center of the beam in mm; and flexural modulus $Y_f=L^3m/4bd^3$, where m is the gradient of the initial load deflection curve in N/mm. Compressive stress is calculated as $\sigma_C=F_C/A$, where $F_C$ is the applied compressive load and A is the original cross-sectional area of the specimen. The strain under compression is defined as $\epsilon_C=(h_0-h)/h_0$, the change in thickness divided by the original thickness of the freestanding specimen, $h_0$. Benchmark figures are noted above.

Data Analysis.

Possible relationships between observable quantities is analyzed by standard methods. For a possible linear relationship involving N points, for instance, both the linear correlation coefficient R and the probability P that N measurements of two uncorrelated variables would give a coefficient at least as large as R will be calculated. P is important for assessing the significance of the apparent relationship. In general, a relationship is considered significant $P\leq 5\%$ and highly significant if $P\leq 1\%$.

EXAMPLES

The information presented herein can be grouped as follows: structure-based differences in polymer processing and material properties, the realization of new material properties from blending dissimilar polypeptides, methods development for materials characterization and structure prediction.

Structure-Based Differences.

Figure 4:
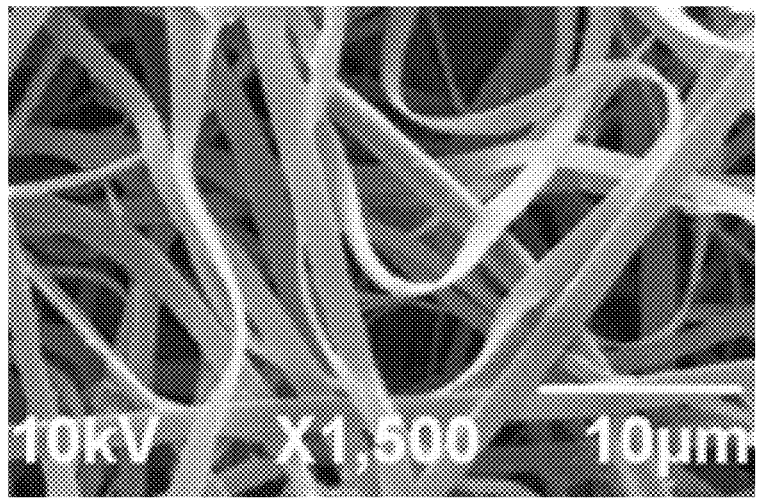
FIG. 4 shows E14 fiber mat morphology by SEM. Nominal feedstock concentration, 55% (w/v) in water. Applied voltage, 10 kV. Spinneretcollector distance, 9 cm. Flow rate, 0.5 µL/min. Unpublished data from the PI's laboratory.

Differences between PLO and PLL and between PLEY and PLGA in relation to spinnability have been previously noted herein. Long fibers of PLEY can be made, but uninterrupted spinning is difficult. Nevertheless, PLEY has proved useful for basic research. Continuous spinning of a novel ELP, "E14", has been demonstrated. In this polymer, which has been produced by recombinant methods, lysine is substituted in for the second valine in 14 out of 50 VPGVG (SEQ ID NO:1) repeat units, and glutamic acid in 2 repeat units. These 16 units are distributed evenly throughout the chain. The DP of E14 is 250. Unlike PLEY, E14 spins into ribbon-like fibers, not cylinders (FIG. 4). This is sufficient proof that polypeptide structure determines fiber morphology. Ribbons result from the formation of an outer shell of solidified polymer before all water has evaporated. When the remaining water evaporates, the cylindrical structure collapses into a ribbon on the fiber collector. Demonstrated differences between PLEY and E14 contribute to a foundation of reproducible empirical data for determining the molecular basis polypeptide behavior in a materials fabrication context.

Figure 5:
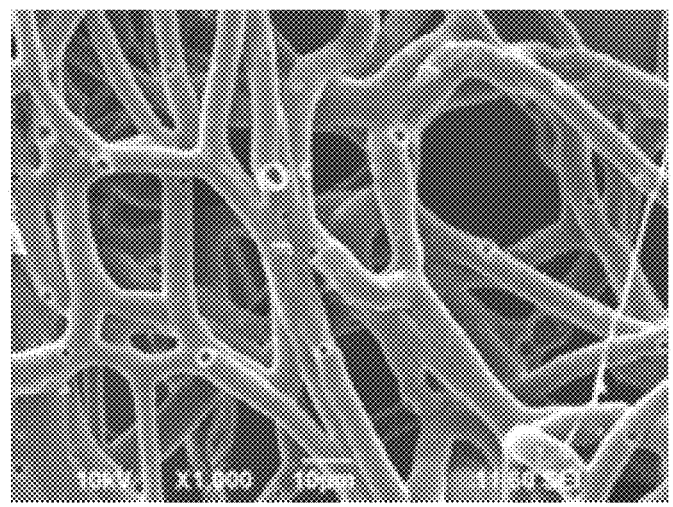
FIG. 5 shows SEM analysis of fibers electrospun from a V40C2:PLEY::2:3 feedstock blend. The nominal final polymer concentration was 48% (w/v). Unpublished data from the laboratory of the PI.

The tin-copper alloy bronze, which is harder than tin or copper, motivated the attempt to blend dissimilar polypeptides and process them in different ways. Results are shown in FIG. 5. Blends of PLEY and V40C2 yielded a fiber morphology not found for either polymer alone. V40C2 is an ELP that contains two VPGCG pentapeptides near the C-terminus of a 50-pentapeptide ELP. The fiber morphology is useful for controlled-release applications. Novel properties can be realized by blending dissimilar polypeptides in an aqueous feedstock.

Characterization Methods.

Figure 6:
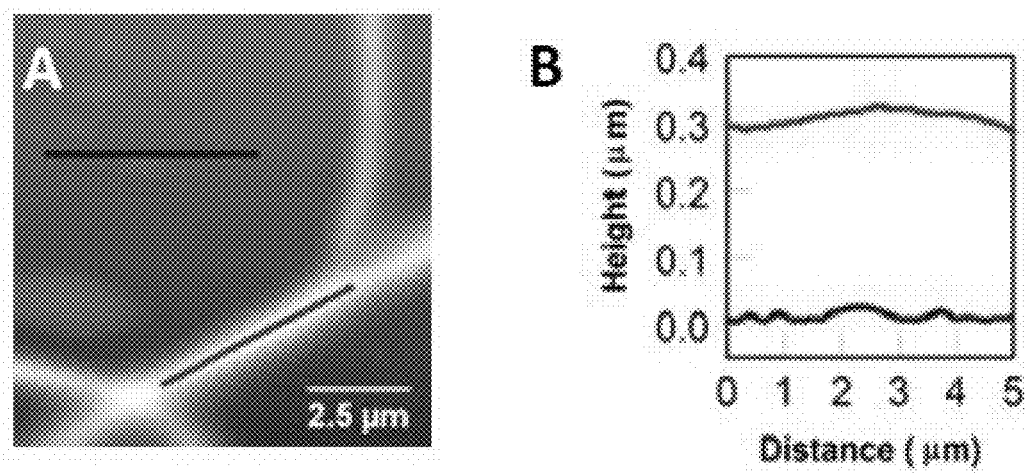
FIG. 6 shows PLEY fiber characterization by AFM. A) 10×10 µm² field of view showing bare glass and fibers. Lines indicate locations of data collection in B). B) Height comparison. Fibers (red) and glass (blue) had a roughness of 1.2 nm and 12.5 nm (standard deviation). Unpublished data from the laboratory of the PI.
Figure 7:
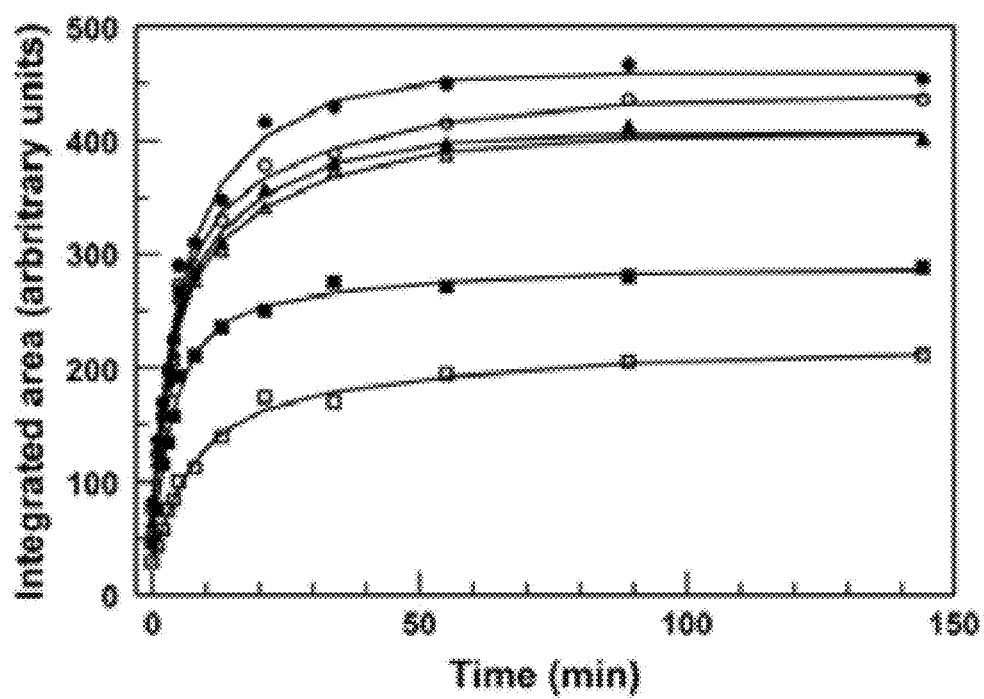
FIG. 7 shows a time series of integrated peak areas for the annealing of PLO fibers. The frequencies analyzed are given in Table 2. Symbols, experimental data points. Solid lines, fitting results. The model function was $P=[1-\exp(-k_a t)]R_{0a}+[1-\exp(-k_b t)]R_{0b}+P0$, where $R_{0a}$ and $R_{0b}$ are the proportions of reactant a and b initially present, $k_a$ and $k_b$ are the rates of formation of $P_a$ and $P_b$ from R, and $P_a$ and $P_b$ are assumed to be indistinguishable from $P_0$, the proportions of product initially present. A sequential pathway model consistently provided a substantially worse fit than a parallel pathways model. Unpublished data from the laboratory of the PI.
Figure 8:
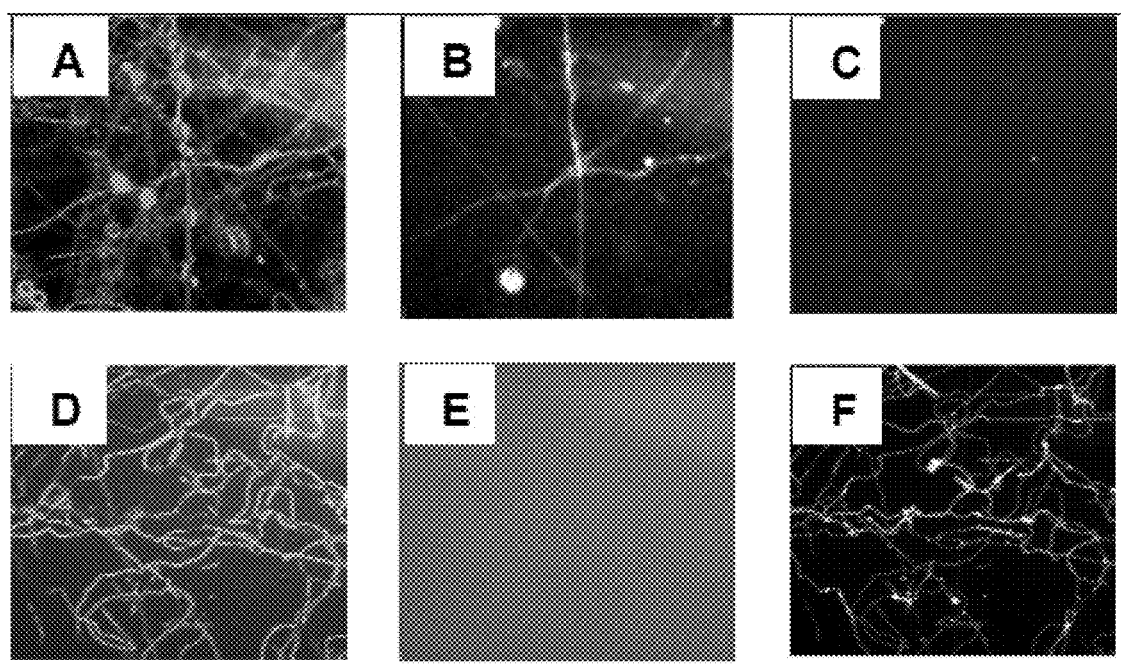
FIG. 8 shows phase separation analysis. Cross-linked PLEY fibers were imaged by (A) bright field, (B) PLEY auto-fluorescence and (C) fluorescein fluorescence microscopy (negative control for FIG. 2F). V40C2:PLEY::1:1 fibers were imaged by (D) bright field, (E) PLEY auto-fluorescence, and (F) fluorescein fluorescence microscopy. Bright field images are displayed inverted and equalized for increased contrast; fluorescence micrographs are not processed. All images were captured with a 10× objective. Unpublished data from the PI's laboratory.
Figure 9:
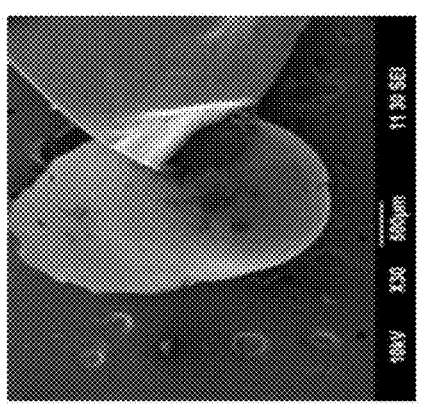
FIG. 9 shows SEM surface analysis of molded PLL cross-linked with GTA. A) 30×, B) 300×, C) 3000×, D) 15,000×. The object on the right in A) is copper tape. The data were obtained by a new PhD student in the PI's laboratory.
Figure 9:
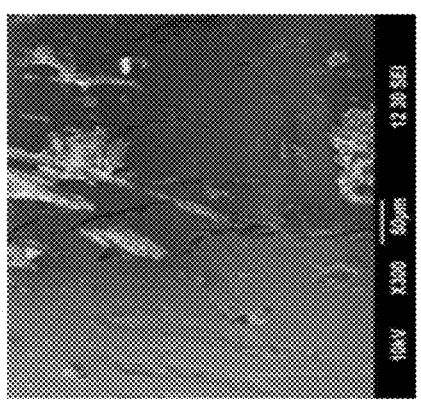
Figure 9:
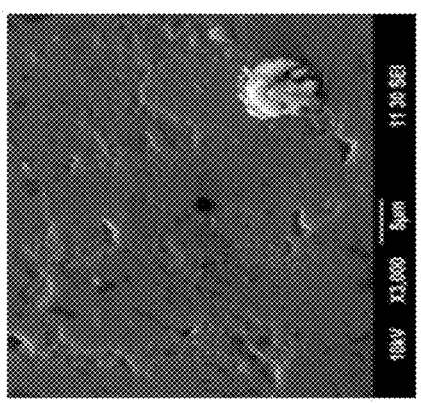
Figure 9:
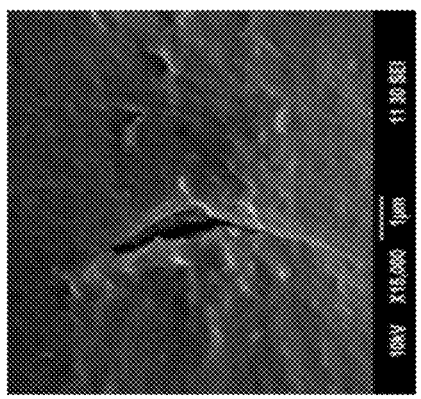

Atomic force microscopy (AFM) is utilized to analyze multilayer films (Zhang et al., 2008) or electrospun fibers (FIG. 6). Further, circular dichroism (CD) spectroscopy is utilized to analyze the structural properties of peptides during multilayer film buildup (Haynie et al., 2005). A concept from multilayer film fabrication is adapted for novel visualization of electrospun fibers by fluorescence microscopy (Khadka et al., 2011). Specifically, FITC-labeled PLL is adsorbed onto cross-linked PLEY fibers in aqueous solution at pH 7. FITC is a fluorescent dye, PLL is positively charged and PLEY is negatively charged at pH 7. Well known chemical methods from biochemistry are adapted for novel analysis of electrospun fibers. For example, a visible-range dye is utilized to quantify the efficiency of crosslinking PLEY (Haynie et al., 2012). The crosslinking reaction consumes free amino groups, and the only amino groups are N-termini. Dye absorbance decreases continuously as the concentration of crosslinking reagent increases after normalizing for fiber mass. The data quantify the percentage of polymers cross-linked. Also, well known physical methods from materials science are adapted for novel analysis of electrospun fiber composition. For example, energy-dispersive X-ray spectroscopy is used to demonstrate the presence of counterions in PLEY fibers and PLO fibers, before and after crosslinking (Haynie et al., 2012 and unpublished data), and the rate of annealing by IR is measured as counterions leach out of cross-linked fibers (FIG. 7 and Table 2). The absence of phase separation in PLEY/V40C2 fibers is demonstrated by fluorescent labeling of the cysteine side chains by maleimide chemistry (FIG. 8). Fiber stiffness prior to collection and crosslinking is apparent from the average radius of curvature of material deposited on glass. According to the theory of continuous materials, the bending energy of a beam is directly proportional to the ratio of the flexural rigidity of the material to the curvature radius squared. This theory is applied to electrospun fibers made of polypeptides by embodiments of the invention described herein. We are the first to obtain light micrographs of biological cells deforming electrospun fibers of any kind, and the first to document it for fibers made of polypeptides (unpublished data). Finally, preliminary cast materials from PLL are made, cross-linked the polymers in situ with GTA and characterized surface properties of the material (FIG. 9).

TABLE 2

Fitting parameters for kinetic modeling of fiber annealing at 22° C.*

| Absorbance band (cm$^{-1}$) | $R_{0a}$ | $\tau_a$ (min) | $R_{0b}$ | $\tau_b$ (min) | $P_0$ |
|---|---|---|---|---|---|
| PLO | | | | | |
| 1339 | 230 | 4.3 | 140 | 31 | 72 |
| 1362 | 120 | 7.1 | 70 | 52 | 28 |
| 1374 | 190 | 4.3 | 60 | 33 | 41 |
| 1475 | 180 | 3.9 | 200 | 16 | 80 |
| 1488 | 200 | 3.4 | 150 | 24 | 56 |
| 1733 | 170 | 3.1 | 170 | 19 | 65 |
| Average | 50 ± 10% | 4.4 ± 0.2 | 35 ± 9% | 29 ± 2 | 15 ± 2% |
| PLEY | | | | | |
| 1339 | 290 | 5.6 | 130 | 51 | 1 |
| 1362 | 150 | 9.1 | 80 | 56 | −11 |
| 1455 | 260 | 5.6 | 210 | 35 | −12 |
| 1490 | 260 | 6.6 | 90 | 86 | −10 |
| 1508 | 390 | 7.2 | 190 | 62 | 20 |
| 1747 | 410 | 7.8 | 100 | 84 | −19 |
| Average | 70 ± 9% | 7.0 ± 0.2 | 32 ± 8% | 63 ± 3 | −2 ± 3% |

*Amplitude averages, percentage mean ± S.D.; time constant averages, mean ± S.E. Unpublished data from the PI's lab.

As to structure prediction, at least three random sequences of 250-residue versions of all of the peptide designs described herein are analyzed with PONDR® VSL2 and PONDR® FIT. VSL2 returns a high level of predicted disorder for nearly every sequence. On a scale of 0-1, predicted disorder is >0.9 for nearly all residues and often >0.99. Some residues in some ELPs had a predicted disorder in the 0.80-0.89 range. In general, though, predicted disorder was nearly maximal for every sequence. There is greater variability in the FIT results. Most sequences have high predicted disorder, but the range was 0.5-1.0. Many sequences have >0.9 predicted disorder at the termini, but 0.5-0.8 in the chain interior. Several titin sequences have 0.3 for many residues in the chain interior. None of the sequences has a significant amount of predicted secondary structure by the Cuff et al. (2000). Predictions were also obtained for the control sequences poly(Gly), poly(Val) and poly(Pro). The only one for which the prediction was anything other than random coil is poly(Val), which is entirely helical apart from four 0 strands at each end. Details of how the predictions are made are provided in Materials and Methods.

Figure 10:
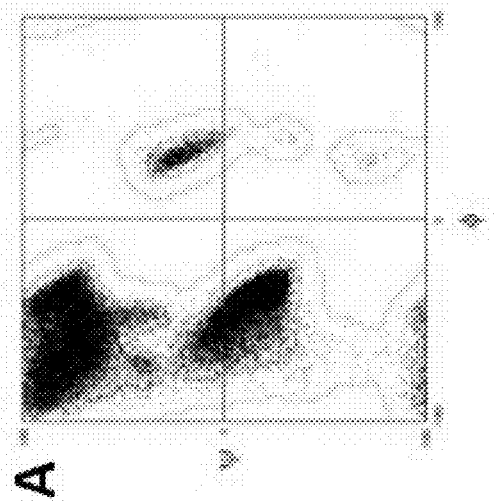
FIG. 10 shows ramachandran plots. Torsion angle $\Psi$ is plotted against $\varphi$. A) Amino acids other than Gly or Pro. B) Gly (symmetrized). C) Pro. Such plots are well known. These are modified from http://kinemage.biochem.duke.edu/validatio n/model.html. ELP has all three types of amino acid.
Figure 10:
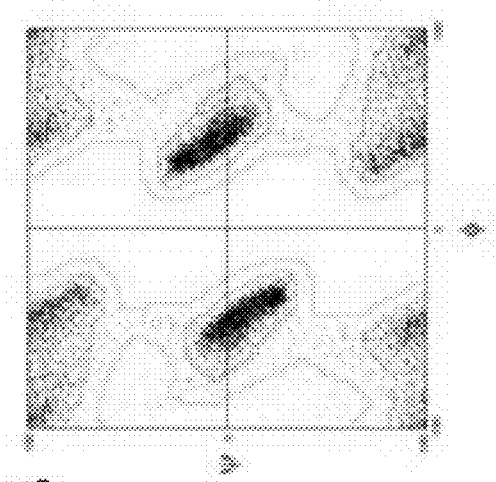
Figure 10:
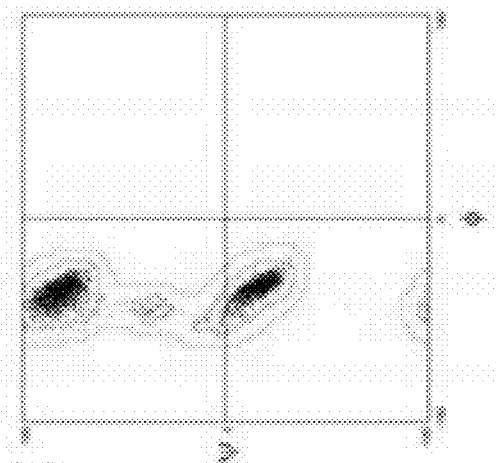

The usual amino acids proline, glycine, alanine, valine, glutamic acid and lysine are particularly valuable for this work. The Ramachandran plot for proline shows that the backbone torsion angles φ and Ψ are very restricted (FIG. 10). This has significant consequences for chain entropy and therefore polymer elasticity (Flory, 1953). In glycine, by contrast, which has no side chain, many more combinations of the torsion angles are possible. This too is significant for chain entropy. The side chain of alanine is a methyl group. This restricts backbone torsion angles, but less so than for proline. Because the small side chain of alanine is free to rotate, it has a high propensity to form α-helical structure (O'Neill and DeGrado, 1990). Valine displays greater torsion angle restrictions than alanine, due to branching in the β carbon of the side chain. In addition, valine side chain has a larger nonpolar surface area than alanine. The glutamic acid side chain is polar and negatively charged at pH 7. The side chain of lysine is polar and positively charged at pH 7. Carboxylic acid groups and amino groups are important for crosslinking. All peptides synthesized also comprise a small mole fraction of tryptophan for assessing polymer concentration by absorbance at 280 nm.

All peptides are prepared by solution-phase synthesis. Target average degree of polymerization values are 20 kDa, 50 kDa and 100 kDa, corresponding to "small", "medium" and "large" proteins. The target range for polydispersity index is 1-1.5. For proteins, polydispersity is usually 1. The comparison with proteins is useful for analyzing some physical properties of synthetic peptides, for instance, viscosity of solution. We determined a) whether the proposed polymer designs can be made and b) the water solubility of each. We also determined c) the molar mass distribution functions by gel permeation chromatography, and from the profile d) the average degree of polymerization and e) polydispersity index of each polymer preparation. It is assumed that electrical conductivity is relevant for electrospinning (Wendorff et al., 2012), so we measured f) the conductivity of each polymer feedstock solution. We determined g) whether one-, two- and three-dimensional materials can be made from the polymers, h) whether the materials can be cross-linked and i) the extent of crosslinking We also determined k) specific physical properties of the materials as indicated below, and l) compared the "processability" and physical properties of each designed peptide with its predicted properties.

For example, PLL is a polypeptide that is not fully processable. This polymer cannot be spun from aqueous solution at any pH value at any degree of polymerization or ionic strength. At basic pH, the polymer precipitates, owing to deionization of the side chains. At neutral or acidic pH, the charge density of the polymer is too high for electrospinning. The same polymer is useful, however, for film casting, multilayer film assembly (Haynie et al., 2004) and molded materials fabrication at pH 7.

Other polypeptides of limited processability are α-keratins and poly(L-alanine) (unless the chains are not more than c. 15 residues long), as these polymers lack the aqueous solubility needed for the materials fabrication approaches of the subject invention. Quantities on which predictions are based are side chain ionization, polar/non-polar surface areas and intrinsic disorder. Nominal side chain pKa values are well established, polar and non-polar solvent-accessible surface areas for amino acids in peptides are well established, and computational methods for predicting intrinsic disorder are available. Details of the approaches are given elsewhere herein.

Randomness of peptides simultaneously makes the synthetic peptides less like native globular proteins and more like the usual synthetic polymers in materials manufacturing and key regions of the elastomeric proteins titin and resilin.

Peptides are synthesized by ring-opening polymerization, characterized in aqueous solution by gel permeation chromatography, viscometry, circular dichroism spectroscopy and other methods, and are processed into 1-, 2- and 3-dimensional materials by several guided self-assembly methods: electrospinning, film casting and molding, and mechanical properties of the materials is then determined by uniaxial tensile strength testing and other methods. An advantage of this approach to synthesis is that no prior knowledge of sequence or persistent secondary or tertiary structure is needed.

Polymer spinnability from aqueous solution predicts processability for film casting and molding. The mechanical properties of elastic proteins has more to do with amino acid composition than sequence, and counterion binding makes a major contribution to the entropic elasticity of peptide materials with ionized side chains.

Four examples are provided. In Example 1, we compare physical properties of random co-polymers of glutamic acid and tyrosine, lysine and tyrosine, and aspartic acid with the corresponding properties of other random polypeptides. In Example 2, we take a novel approach to the analysis of elastin-like peptide (ELP). In Example 3, we apply the approach of Example 2 to collagen, titin and resilin, other elastomeric proteins. In Example 4, we demonstrate fundamental aspects of the role of the polymer backbone in entropic elasticity.

An important practiced aspect of the subject invention is that polypeptide processing as outlined here can be done at ambient temperature under mild solution conditions, and the materials will be biodegradable. We also emphasize polymer solubility in water and the possibility of eliminating or reducing the amount of organic solvent needed in materials manufacturing.

Example 1—PLEY, PLKY and PLAA

As noted above, spinnability predicts processability for film casting and for molding. Electrospinning designed polypeptides are advantageous not only for producing fibrous materials, but also for diagnosing suitability for other kinds of materials.

Properties of PLEY are known from experimental study (Khadka et al., 2011; Haynie et al., 2012; Haynie et al., 2013; Khadka et al., unpublished data). PLEY is 80% Glu; PLGA is all Glu (Table 4). PLEY is spinnable; PLGA is not spinnable at any DP, concentration or ionic strength (Khadka et al., 2011; Haynie et al., 2012). PLGA thus resembles PLL, which is not spinnable even though PLO is spinnable. Asp differs from Glu by just a single methylene group in the side chain, just like Orn and Lys. It is expected, then, that PLAA is less ionized than PLGA and the electrostatic potential of PLAA is reduced by deprotonation at pH 7. The same reasoning probably explains why PLO is spinnable but PLL is not.

Method.

Synthetic PLEY, PLGA, PLKY and PLL are sold by commercial sources. The only compositions of PLEY and PLKY available, however, are 20% tyrosine, barring custom synthesis, which is expensive. Polypeptides are synthesized for systematic study of PLEY at different mole ratios of tyrosine. We have studied Glu:Tyr::4:1 in previous work (Khadka et al., 2011; Haynie et al., 2012; Haynie et al., 2013). Here, 19:1, 9:1, 17:3, 4:1, 3:1, 7:3, 13:7, 3:2 and 1:1 is analyzed for comparison. PLKY, poly(L-Asp, L-Tyr) (PLDY) and poly(L-Orn, L-Tyr) (PLOY) are also made in the same mole ratios. PLAA is synthesized. It is expected that PLKY, PLAA, PLDY and PLOY can be made in solution because PLL, PLGA, PLO and PLEY are made that way. Details of synthesis are outlined in Materials and Methods, herein above. How the polymers and polymer solutions are characterized is summarized in Table 3. See Materials and Methods for further details. How materials are characterized is summarized in Table 4. PLEY, PLAA and PLDY is cross-linked with EDC in 90% ethanol. PLKY and PLOY is cross-linked with GTA vapor. See Materials and Methods for crosslinking details.

TABLE 3

How polymer solutions are characterized

| Property | Approach and tool | Location |
| --- | --- | --- |
| Amino acid composition | Acid hydrolysis, amino acid analysis by HPLC | Peptide Synthesis Facility, Chemistry, USF |
| Average DP | Ostwald viscometry, gel permeation chromatography | Apparatus applied for here, Chemistry, USF |
| Hydrodynamic radius | DLS at 633 nm | Physics, USF |
| Polydispersity index | Gel permeation chromatograph | Chemistry, USF |
| Solubility | Turbidity at 330 nm, spectrophotometer | Laboratory of PI |
| Viscosity | Ostwald viscometry | Apparatus applied for here |
| Conductivity | Conductivity meter | Laboratory of PI |
| Polymer structure | CD spectroscopy | Peptide Synthesis Facility, Chemistry, USF |
| Chain entanglement | UV spectroscopy and DLS, guanidine hydrochloride | Laboratory of the PI. Optical Characterization Lab., Physics, USF |

TABLE 4

How polymer-based materials are characterized

| Property | Approach and tool | Location |
| --- | --- | --- |
| Elemental composition | EDX | JEOL SEM in the physics department |
| Crosslinks per polymer | Chemical modification and absorbance | Jasco UV spectrometer in the laboratory of the PI |
| Birefringence | Polarizing microscopy | Microscope in Department of Integrative Biology at USF |
| Average polymer conformation | PTIR-ATR | Jasco IR spectrometer in the laboratory of the PI |
| Surface morphology | Critical-point drying, SEM, AFM | Critical-point dryer in medical school, SEM in Physics, AFM in the Nanotechnology Research and Education Center, all at USF |
| Microscopic tensile strength | Single fiber analysis | Apparatus applied for here |
| Macroscopic tensile strength | Universal tester | Apparatus applied for here |

Spinnable polymers are processed at counterion concentrations up to 1 M and, after crosslinking, fibers are submersed in aqueous solutions at counterion concentrations up to 1 M. The counterions are Na+ and Br−, depending on the sign of charge of side chains, as in prior work (e.g. Haynie et al., 2012). In aqueous media the association and dissociation of ions is primarily entropic, as in typical high-affinity ion binding to proteins. The enthalpic contribution is small because, in typical cases, ion binding does not involve the complete removal of hydrating water molecules. Evidence is provided by α-lactalbumin, for example, which binds $Ca^{2+}$ with nM affinity. Several water molecules are coordinated to the ion in the binding pocket, according to X-ray diffraction analysis (Acharya et al., 1989). Changes in ion association can therefore translate into an entropic contribution to elasticity. Contributions to elasticity of this sort are not possible in materials made of typical synthetic organic polymers, which have no ionized side chains and so no counterions bound. At the same time, however, peptide materials certainly still display entropic elasticity due to chain extensibility, albeit less so than for polymers like polyethylene, because there are no rotations about the peptide bond at 300 K and the amide group is a hydrogen bond donor. The propensity to form stable secondary structure is minimized here by focusing on random sequences. This minimizes the possible influence of secondary structure formation on elasticity.

Data Analysis.

Example 1 not only determines polymer spinnability for different polypeptides, it also enables testing of the predictability of polymer properties on the basis of amino acid composition, side chain ionization and solvent-accessible surface areas and helps ensure that the selected characterization methods are ready for Examples 2-4. Polymer properties are predicted as outlined in the Materials and Methods, herein above. Elasticity and other mechanical properties are determined as outlined in the Materials and Methods. Experimental data is used to gauge the reliability of the predictions as described above and below.

Results.

Example 1 reveals for PLEY and PLKY which mole ratios of Tyr can be synthesized and are spinnable, and whether PLAA, PLDY and PLOY can be synthesized and spun. The subject invention thus advances basic knowledge of peptide synthesis and aqueous solubility, clarifies structure requirements for electrospinning and yields novel polymers for other approaches to materials fabrication. In instances of difficulty in crosslinking PLEY, PLAA or PLDY at 50 mM EDC, as indicated in the Materials and Methods, one can increase the concentration to as high as 200 mM (Haynie et al., 2012). If it is difficult to crosslink PLKY or PLOY with GTA vapor, one can increase the concentration of GTA from 25% to as high as 75% (unpublished data). Alternatively, the crosslinking reaction time is increased.

The stiffness of a material varies with the number of crosslinks per unit mass of polymer (Flory, 1953), and electrostatic interactions and hydrophobic interactions between polymers influences stiffness and other physical properties, whether the materials are hydrated or not. Increasing the number of attractive electrostatic interactions per unit mass of cross-linked polypeptides influences both entropic and enthalpic contributions to elasticity, depending on the counterions bound and hydration. Analysis of these contributions to elasticity, is enabled by comparative analysis of amino acid composition. Ionized side chains not involved in crosslinking can coordinate small ions, as in PLEY and PLO (Haynie et al., 2012). Binding must be energetically favorable if it occurs at equilibrium, so ion pair formation must increase fiber rigidity. If the pairs are readily severed by applying an external force, which is assumed to be the case for small counterions and a high level of hydration, then ion binding will also influence elasticity. Ionic strength is an important means of controlling the physical properties of peptide-based materials.

Example 2—ELP

This example uniquely combines ELP, sequence randomization and lysine. Various other amino acids are substituted for Lys to demonstrate alternative methods of crosslinking.

Elastin plays a key role in determining the mechanical properties of skin and other tissues. The structure and function of the protein have been studied extensively by various investigators. There have been numerous studies on ELPs, that is, (VPGVG)n-based peptides ((SEQ ID NO: 1)n-based peptides), where V is valine, P is proline and G is glycine. VPGVG (SEQ ID NO:1) is a repeat unit in wild-type elastin. The most common approach to structure modification in ELP research has been to substitute any amino acid besides P or V for X in VPGXG, and for some mole fraction of such pentapeptides relative to VPGVG (SEQ ID NO:1) to occur in the same polymer prepared by recombinant methods. The present invention differs from all previous ELP work in several significant ways. One, the focus is on random sequences, not repeats of VPGXG. No one has studied random sequences of ELP before. Two, the relative proportions of V, G and P are preserved throughout; they are always 2:2:1 here. In previous research, the proportion of V relative to G and P changed with the mole fraction of VPGXG, X≠V. Three, the present peptides are polydisperse, and the sequences are different. In previous research, ELPs were produced by recombinant synthesis or solid-phase synthesis. In short, the current invention methods are more akin to polymer synthesis for materials fabrication than in any previous studies of ELP or other structural proteins. Four, it is not clear from existing evidence whether the repetitive wild-type sequence of elastin is more an artifact of gene duplication than an amino acid composition or sequence optimized for elasticity. No one has addressed this question before to the best of our knowledge, and surely not as described here.

The random sequence approach of this invention is advantageous because scrambling the sequence will surely destroy the ability of the polymers to form 13 spirals in aqueous solution [Urry (2006) and references cited therein]. Spiral formation depends on proline, which distorts the polymer backbone and limits torsion angle space (FIG. 10) periodically along the chain. Proline residues are redistributed in random peptides, enabling a direct comparison with ELP in various respects, e.g., average conformation in solution, viscosity as a function of concentration and mechanism of elasticity. It is crucial for material properties that random polypeptides are less likely than repetitive polymers to pack uniformly in a solid material. Random polypeptides are therefore more likely to display purely entropic elasticity. Purely entropic elasticity is desirable because of its high efficiency for converting elastic into mechanical energy. The insect protein resilin provides a supporting example (Elvin et al., 2005).

Method.

ELPs are synthesized in solution. The amino acid composition is 2:2:1::Val:Gly:Pro, as in ELPs studies performed previously. Unique features of the present peptides are random sequence, polydispersity and sequence variability. The average DP of the polymers is ~250, roughly 22 kDa, for the sake of comparison with V40C2. The percentage Lys is varied systematically in 10% increments, from 0-30% (Table 5). The upper limit coincides (roughly) with the percentage of Val and Gly. All ELPs are expected to be soluble, because ELP is soluble in the absence of Lys and these side chains are ionized in water at pH 7. Unlike previous work, Val:Gly:Pro::2:2:1 is maintained for all the peptides in Table 5. The properties of these peptides is compared and contrasted with ELP, PLEY and the other peptides of Example 1. In any case, polymers of roughly 50 kDa and 100 kDa are synthesized for the sake of comparison with the lower-mass polymers. Once random sequences of Val:Gly:Pro::2:2:1 are made as in Table 5 and characterized, random sequences of variable composition are made as in Table 6 and characterized. Finally, selected blends of these polymers and those of Example 1 are made. For example, ELP-K30 is blended with PLKY 19:1. It is possible to crosslink these polymers with GTA vapor, as indicated by the data in FIG. 8. An indication of the novel structures blending yields is provided by data for PLEY/V40C2 (FIG. 5). The approach taken here for Lys is applied to Arg, Asp, Glu, cysteine (Cys) and histidine (His). The rationale for these choices is as follows. Arg is positively charged at pH 7, like Lys, but it cannot be cross-linked with an aldehyde. This enables a direct comparison with Lys on the basis of side chain structure. Asp and Glu are, like Lys, ionized at pH 7, but the sign of charge is the opposite. This enables a direct comparison with Lys on the basis of sign of charge. Asp differs from Glu by a single methylene group in the aliphatic part of the side chain. This enables a direct comparison with Glu on the basis of side chain structure. Cys can form crosslinks called disulfide bonds. The rate of reaction between two Cys side chains is increased under mild oxidizing conditions, especially in the presence of trace amounts of metal ions. The relative abundance of Cys should exceed 2/250, based on preliminary results from the inventors' laboratory (Khadka et al., manuscript in preparation). Finally, His has a pKa of ~6.5. Inclusion of His therefore confers pH sensitivity on materials near pH 7.

TABLE 5

Test compositions for lysine in ELP

| Identification | Valine (Val, V) | Glycine (Gly, G) | Proline (Pro, P) | Lysine (Lys, K) |
| --- | --- | --- | --- | --- |
| ELP-K0 | 40 | 40 | 20 | 0 |
| ELP-K10 | 36 | 36 | 18 | 10 |
| ELP-K20 | 32 | 32 | 16 | 20 |
| ELP-K30 | 28 | 28 | 14 | 30 |

TABLE 6

Tests compositions based on ELP

| Identification | Val | Gly | Pro | Predicted properties |
| --- | --- | --- | --- | --- |
| ELP-1 | 50 | 30 | 20 | Insoluble, ordered |
| ELP-2 | 40 | 40 | 20 | Soluble, wild-type, ordered |
| ELP-3 | 30 | 50 | 20 | Soluble |
| ELP-4 | 60 | 40 | 0 | Insoluble, ordered |
| ELP-5 | 50 | 50 | 0 | Insoluble, ordered |
| ELP-6 | 40 | 60 | 0 | Possibly soluble, ordered |
| ELP-7 | 40 | 20 | 40 | Possibly insoluble, ordered |
| ELP-8 | 30 | 30 | 40 | Soluble |
| ELP-9 | 20 | 40 | 40 | Soluble |

Data Analysis.

Same as for Example 1.

ELP has been selected as a convenient and useful bio-inspired starting point for assessing boundaries on polypeptide processability. Example 2 determines to what extent a random sequence of the corresponding sequence composition reproduces key material properties of a given sequence. Elasticity is included among these properties.

Example 3—Structural Proteins Other than Elastin

As in Example 2, the peptide structures are bio-inspired, being based on the sequences of resilin, collagen and other structural proteins.

Method.

The approach outlined in Example 2 is not specific to ELP; other elastic proteins are known. Essentially the same approach as in Example 2 is therefore applied for essential features of the known amino acid compositions of α-keratin, β-keratin, spider silk, collagen (a connective tissue protein), resilin and titin (an elastic protein in skeletal muscle). These polymers have a high percentage of valine (Val), glycine (Gly), alanine (Ala) and proline (Pro). Physical properties of the noted proteins are known from extensive experimental study by other investigators, for example, Elvin et al. (2005). In elastin, Lys residues occur between Pro-rich segments. The side chains of these Lys residues are enzymatically cross-linked in neighboring chains, forming an elastic network. In the titin polypeptide, which gives striated muscle its elasticity, there is a region abundant in Pro, Glu, Val and Lys (the PEVK region). This region provides elasticity at moderate levels of force (Linke et al., 1998). When relaxed, the PEVK region is compact but lacks folded structure. Pulling results in stretching. The availability of ion binding sites in titin varies with tension, so how ions will influence the entropic elasticity of titin is a function of the applied force and the ionic strength of the surrounding medium. The same basic concept can be applied to the materials of this invention. If Pro follows Gly, more degrees of freedom will be lost than if Pro follows Val. Representative amino acid compositions for this work are shown in Tables 7-9.

Data Analysis.

Same as for Example 1.

TABLE 7

Tests compositions based on collagen

| Identification | Gly | Pro | Ala | Lys |
|---|---|---|---|---|
| COL-1 | 60 | 20 | 20 | 0 |
| COL-2 | 54 | 18 | 18 | 10 |
| COL-3 | 48 | 16 | 16 | 20 |
| COL-4 | 42 | 14 | 14 | 30 |
| COL-5 | 36 | 12 | 12 | 40 |
| COL-6 | 30 | 10 | 10 | 50 |

TABLE 8

Tests compositions based on resilin

| Identification | Gly | Pro | Lys |
|---|---|---|---|
| RES-1 | 90 | 5 | 5 |
| RES-2 | 85 | 5 | 10 |
| RES-3 | 80 | 10 | 10 |
| RES-4 | 75 | 10 | 15 |
| RES-5 | 70 | 15 | 15 |
| RES-6 | 65 | 15 | 20 |

TABLE 9

Tests compositions based on titin

| Identification | Val | Pro | Lys | Glu |
|---|---|---|---|---|
| TTN-1 | 25 | 25 | 25 | 25 |
| TTN-2 | 25 | 25 | 35 | 15 |
| TTN-3 | 25 | 25 | 45 | 5 |
| TTN-4 | 25 | 35 | 20 | 20 |
| TTN-5 | 25 | 45 | 15 | 15 |
| TTN-6 | 35 | 25 | 20 | 20 |
| TTN-7 | 45 | 25 | 15 | 15 |

Example 4—Limits on Polymer Backbone Properties

The peptide structures of this example are not particularly bio-inspired. Elastin, resilin, titin and other structural proteins contain a much larger percentage of glycine (Gly), proline (Pro) and alanine (Ala) than globular proteins, and these are the amino acids of focal interest in this example.

Method.

The following steps are taken. 1) Fix the percentage Glu at 80% for the sake of processability and then systematically vary the percentage of Ala, Gly, Pro and Val at 20% (Table 10). In this context Val is a kind of control, though of course it is also found in abundance in ELP (Example 2) and titin (Example 3). Tyr is also included for the sake of comparison with PLEY (Example 1). 2) Fix the percentage of glutamic acid at 60% and systematically vary the percentage of Ala, Gly, Pro, Val and Tyr at 40%. 3) Substitute Lys for Glu and repeat 1) and 2) to demonstrate the relevance of sign of charge.

Data Analysis.

Same as for Example 1.

The focus here is the polymer backbone. This distinguishes contributions from side chains and backbones. The role of charge is presumably independent of amino acid composition. Reproducible differences for different polymer preparations are due to amino acid composition.

TABLE 10

Tests compositions for polymer backbone properties

| Identification | Glu | Ala | Gly | Pro | Val | Tyr |
|---|---|---|---|---|---|---|
| BB-E80-1 | 80 | 20 | 0 | 0 | 0 | 0 |
| BB-E80-2 | 80 | 0 | 20 | 0 | 0 | 0 |
| BB-E80-3 | 80 | 0 | 0 | 20 | 0 | 0 |
| BB-E80-4 | 80 | 0 | 0 | 0 | 20 | 0 |
| BB-E80-5 | 80 | 0 | 0 | 0 | 0 | 20 |

Predicted properties of polymers are compared with actual outcomes in aqueous solution and in solids. The comparisons enable the articulation of relationships, in some cases, mathematical formulas, for predicting peptide processability under the constraints of amino acid composition, DP, pH and ionic strength. Processability, as defined here, encompasses not only polymer synthesis, but also solubility, structure in aqueous solution, processing for 1-, 2- and 3-dimensional materials fabrication, chemical crosslinking and physical properties such as elasticity. The relationships account for key quantitative features of the polymers, including side chain ionizability, polar and non-polar solvent-accessible surface areas and propensity to form secondary structures. The invention thus delivers a means of making meaningful comparisons of material properties between the subject random peptides, protein correlates and non-peptide elastomers. Target values of physical properties are noted in Materials and Methods, herein above.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

Acharya, K. R., Stuart, D. I., Walker, N. P. C., Lewis, M. and Phillips, D. C. (1989) Refined structure of baboon α-lactabumin at 1.7 Å resolution: Comparison with C-type lysozyme, *J. Mol. Biol.* 208:99-127.

Aliferis, T., Iatrou, H. and Hadjichristidis, N. (2004) Living polypeptides, *Biomacromolecules* 5:1653-1656.

Berger, A., Kurtz, J. and Katchalski, E. (1954) Poly-L-proline, *J. Am. Chem. Soc.* 76:5552-5554. Boal, D. (2012) *Mechanics of the Cell* 2ed (Cambridge: Cambridge University Press) ch. 3.

Bray, B. L. (2003) Large-scale manufacture of peptide therapeutics by chemical synthesis, *Nat. Rev. Drug. Disc.* 2:587-593.

Chawla, K. K. (2005) *Fibrous Materials* (Cambridge: Cambridge University Press).

Chow, G.-M., Ovid'ko, I. A. and Tsakalakos, T. eds (2000) *Nanostructured Films and Coatings*. NATO Science Partnership Subseries: 3 (Dordrecht, The Netherlands: Kluwer).

Creighton, T. E. (1994) *Proteins: Structures and Molecular Properties* (New York: Freeman).

Cuff, J. A., Birney, W., Clamp, M. E. and Barton, G. J. (2000) ProtEST: protein multiple sequence alignments from expressed sequence tags, *Bioinformatics* 16:111-116.

Dawson, R. M. C., Elliott, D. C., Elliott, W. H. and Jones, K. M. (1986) *Data for Biochemical Research* 3ed (Oxford: Oxford University Press).

Deming, T. and Curtin, S. A. (2000) Chain initiation efficiency in cobalt- and nickel-mediated polypeptide synthesis, *J. Am. Chem. Soc.* 122:5710-5717.

Dill, K. A. and Bromberg, S. (2010) *Molecular Driving Forces: Statistical Thermodynamics in Biology, Chemistry, Physics, and Nanoscience* 2ed (New York: Garland).

Elvin, C. M., Carr, A. G., Huson, M. G., Maxwell, J. M., Pearson, R. D., Vuocolo, T., Liyou, N. E., Merritt, D. J. and Dixon, N. E. (2005) Synthesis and properties of cross-linked recombinant pro-resilin, *Nature* 437:999-1002.

Fasman, G. D. and Blout, E. R. (1963) Polypeptides. XLI. High molecular weight poly-L-proline: Synthesis and physical-chemical studies, *Biopolymers* 1:3-14.

Finkelstein, A. V. and Ptitsyn, O. B. (2002) *Protein Physics* (New York: Academic).

Flory, P. J. (1953) *Principles of Polymer Chemistry* (Ithaca: Cornell University Press).

Fudge, D. S. and Gosline, J. M. (2004) Molecular design of the -keratin composite: insights from a matrix-free model, hagfish slime threads, *Proc. Roy. Soc. Lond. B* 271:291-299.

Gill, S. C. and von Hippel, P. H. (1989) Calculation of protein extinction coefficients from amino acid sequence data, *Anal. Biochem.* 182:319-326.

Haynie, D. T. (2008) *Biological Thermodynamics* 2ed (Cambridge: Cambridge University Press).

Haynie, D. T. and Freire, E. (1993) Structural energetics of the molten globule state, *Proteins: Struct., Func., Genet.* 16:115-140.

Haynie, D. T., Khadka, D. B. and Cross, M. C. (2012) Physical properties of polypeptide electrospun nanofiber cell culture scaffolds on a wettable substrate, *Polymers* 4:1535-1553.

Haynie, D. T., Khadka, D. B., Cross, M. C., Gitnik, A. and Le, N. K. (2013) Mechanisms of stability of fibers electrospun from peptides with ionized side chains, *Macromol. Mater. Eng.* 5:529-540.

Haynie, D. T., Balkundi, S., Palath, N., Chakravarthula, K., and Dave, K. (2004) Polypeptide multilayer films: Role of molecular structure and charge, *Langmuir* 20:4540-4547.

Haynie, D. T., Palath, N., Liu, Y., Li, B. and Pargaonkar, N. (2005) Biomimetic nanotechnology: Inherent reversible stabilization of polypeptide microcapsules, *Langmuir* 21:1136-1138.

Howard, J. (2001) *Mechanics of Motor Proteins and the Cytoskeleton* (Sunderland, Mass.: Sinauer Associates) p. 31.

Hsin, J., Strümpfer, J., Lee, E. H. and Schulten, K. (2011) Molecular origin of the hierarchical elasticity of titin: simulation, experiment, and theory, *Annu. Rev. Biophys.* 40:187-203.

Khadka, D. B., Cross, M. C. and Haynie, D. T. (2011) A synthetic polypeptide electrospun biomaterial, *ACS Appl. Mater. Interfaces* 3:2994-3001.

Khadka, D. B. and Haynie, D. T. (2010) Insoluble synthetic polypeptide mats from aqueous solution by electrospinning, *ACS Appl. Mater. Interfaces* 2:2728-2732.

Khadka, D. B. and Haynie, D. T. (2012) Protein- and peptide-based electrospun nanofibers in medical biomaterials, *Nanomedicine: NBM* 8:1242-1262.

Kim, K. Y., Komoto, T. and Kawai, T. (1979) Crystallization of poly(L-proline) in the course of polymerization, *Makromol. Chem.* 180:465-472.

Li, D., Wang, Y. L. and Xia, Y. N. (2003) Electrospinning of polymeric and ceramic nanofibers as uniaxially aligned arrays, *Nano Lett.* 3:1167-1171.

Linke, W. A., Ivemeyer, M., Mundel, P., Stockmeier, M. R. and Kolmerer, B. (1998) Nature of PEVK-titin elasticity in skeletal muscle, *Proc. Natl Acad. Sci. (USA)* 95:8052-8057.

Lu, H. and Cheng, J. (2007) Hexamethyldisilazane-mediated controlled polymerization of—amino acid-N-carboxyanhydrides, *J. Am. Chem. Soc.* 129:14114-14115.

Nagapudi, K., Brinkman, W. T., Leisen, J. E., Huang, L., McMillan, R. A., Apkarian, R. P., Conticello, V. P. and Chaikof, E. L. (2002) Photomediated solid-state cross-linking of an elastin-mimetic recombinant protein polymer, *Macromolecules* 35:1730-1737.

Nicholson, J. W. (2006) *The Chemistry of Polymers* 3ed (Cambridge: The Royal Society of Chemistry).

O'Neill, K. T. and DeGrado, W. F. (1990) Side chain contributions to the stabilities of alpha-helical structure in peptides, *Science* 250:669-673.

Osaki, S. (2012) Spider silk violin strings with a unique packing structure generate a soft and profound timbre, *Phys. Rev. Lett.* 108:154301-154306.

Peng, K., Radivojac, P., Vucetic, S., Dunker, A. K. and Obradovic, Z. (2006) Length-dependent prediction of protein intrinsic disorder, *BMC Bioinformatics* 7:208.

Peng, K., Vucetic, S., Radivojac, P., Brown, C. J., Dunker, A. K. and Obradovic, Z. (2005) Optimizing long intrinsic disorder predictors with protein evolutionary information, *J. Bioinform. Comput. Biol.* 3:35-60.

Peng, Y., Lai, S. and Lin, C. (2008) Preparation of polypeptide via living polymerization of Z-Lys-NCA initiated by platinum complexes, *Macromolecules* 41:3455-3459.

Petka, W. A., Harden, J. L., McGrath, K. P., Wirtz, D. and Tirrell, D. A. (1998) Reversible hydrogels from self-assembling artificial proteins, *Science* 281:389-392.

Regan, L. and DeGrado, W. F. (1988) Characterization of a helical protein designed from first principles, *Science* 241:976-978.

Romero, P., Obradovic, Z., Li, X., Garner, E. C., Brown, C. J. and Dunker, A. K. (2001) Sequence complexity of disordered protein, *Proteins: Struct., Func., Genet.* 42:38-48.

Shen, Z. L., Dodge, M. R., Kahn, H., Ballarini, R. and Eppell, S. I. (2008) Stress-strain experiments on individual collagen fibrils, *Biophys. J.* 95:3956-3963.

Strobl, G. (2007) *The Physics of Polymers: Concepts for Understanding Their Structures and Behavior* 3ed (Berlin: Springer).

Tadmor, Z. and Gogos, C. G. (2006) *Principles of Polymer Processing* 2ed (Hoboken: Wiley).

Tan, E. P. S., Ng, S. Y. and Lim, C. T. (2005) Tensile testing of a single ultrafine polymeric fiber, *Biomaterials* 26:1453-1456.

Tanford, C. (1961) *Physical Chemistry of Macromolecules* (New York: Wiley).

Tanford, C., Kawahara, K. and Lapanje, S. (1967) Proteins as random coils: I. Intrinsic viscosities and sedimentation coefficients in concentrated guanidine hydrochloride, *J. Am. Chem. Soc.* 89:729-736.

Thayer, A. M. (2011) Making peptides at large scale, *Chem. Eng. News* 89:21-25.

Urry, D. W. and Parker, T. M. (2002) Mechanisms of elastin: molecular mechanism of biological elasticity and its relationship to contraction, *J. Muscle Res. Cell Motil.* 23:543-549.

van Beek, J. D., Hess, S., Vollrath, F. and Meier, B. H. (2002) The molecular structure of spider dragline silk: folding and orientation of the protein backbone, *Proc. Natl Acad. Sci. (USA)* 99:10266-10271.

Vincent, J. F. V. and Wegst, U. G. K. (2004) Design and mechanical properties of insect cuticle, *J. Muscle Res. Cell Motil.* 23:543-559.

Voet, D., Voet, J. G. and Pratt, C. W. (2006) *Fundamentals of Biochemistry: Life at the Molecular Level* (New York: Wiley).

Weis-Fogh, T. and Andersen, S. O. (1970) New molecular model for the long-range elasticity of elastin, *Nature* 277:718-721.

Wendorff, J. H., Agarwal, S. and Greiner, A. (2012) *Electrospinning* (Weinheim: Wiley-VCH).

Wetlaufer, D. B. and Xie, Y. (1995) Control of aggregation in protein refolding: A variety of surfactants promote renaturation of carbonic anhydrase II, *Prot. Sci.* 4:1535-1543.

Wimley, W. C., Creamer, T. P. and White, S. H. (1996) Solvation energies of amino acid side chains and backbone in a family of host-guest pentapeptides, *Biochemistry* 35:5109-5124.

Xue, B., Dunbrack, R. L., Williams, R. W., Dunker, A. K. and Uversky V. N. (2010) PONDR-FIT: A metapredictor of intrinsically disordered amino acids, *Biochim. Biophys. Acta Prot. Proteomics* 1804:996-1010.

Zhang, L., Zhao, W., Rudra, J. S. and Haynie, D. T. (2008) Context dependent fabrication, structure, stability and disassembly of polypeptide multilayer nanofilms, *ACS Nano* 1:476-486.

Zhang, S. (2003) Fabrication of novel biomaterials through molecular self-assembly, *Nat. Biotechnol.* 21:1171-1178.

---

---

We claim:

1. A peptide-based material, comprising cross-linked peptides with random amino acid sequences that are soluble in water or ethanol before crosslinking but insoluble in water after crosslinking, wherein the cross-linked peptides are elastin-like peptides (ELPs), wherein each ELP sequence comprises lysine substituted in for the second valine in 14 out of 50 VPGVG (SEQ ID NO:1) repeat units, provided that the proportions of valine (V):glycine (G):proline (P) are 2:2:1 in each ELP sequence.

2. The peptide-based material of claim 1, further comprising synthetic organic polymers.

3. The peptide-based material of claim 1, wherein the cross-linked peptides are synthesized by ring-opening polymerization.

4. The peptide-based material of claim 1, wherein the material is a disposable material.

5. The peptide-based material of claim 4, wherein the disposable material is a biodegradable material.

6. The peptide-based material of claim 1, wherein the material is a cell culture scaffolding material.

7. The peptide-based material of claim 1, wherein the material is a foam material.

8. The peptide-based material of claim 1, wherein the material is a one-dimensional material.

9. The peptide-based material of claim 8, wherein the one-dimensional material is a fiber material.

10. The peptide-based material of claim 9, wherein the material is an anti-microbial fiber material.

11. The peptide-based material of claim 1, wherein the material is a two-dimensional material.

12. The peptide-based material of claim 11, wherein the two-dimensional material is a film material.

13. The peptide-based material of claim 12, wherein the material is a medical device coating film material.

14. The peptide-based material of claim 1, wherein the material is a three-dimensional material.

15. The peptide-based material of claim 14, wherein the three-dimensional material is a molded material.

* * * * *

UNITED STATES PATENT AND TRADEMARK OFFICE
CERTIFICATE OF CORRECTION

PATENT NO. : 9,932,443 B2
APPLICATION NO. : 14/561413
DATED : April 3, 2018
INVENTOR(S) : Donald T. Haynie It is certified that error appears in the above-identified patent and that said Letters Patent is hereby corrected as shown below:

Column 3,
Line 5, "made by solidphase synthesis," should read --made by solid-phase synthesis,--.

Column 4,
Line 56, "Spinneretcollector distance, 9 cm." should read --Spinneret collector distance, 9 cm.--.

Column 6,
Lines 32-33, "6 side-chains+1 N-terminal a)." should read --6 side-chain ε + 1 N-terminal α).--.

Column 15,
Line 28, "limits are 0 and co." should read --limits are 0 and ∞.--.

Column 16,
Lines 4-5, "[η]=K'$R_G^3$/M; K" and K'" should read --[η] = K"$R_G^3$/M; K'" and K"--.
Line 5, "better than a 0" should read --better than a θ--.
Line 6, "K and a are" should read --K' and α are--.
Line 7, "K and a are" should read --K' and α are--.
Line 61, "ellipticity per residue [0]" should read --ellipticity per residue [θ]--.
Line 63, "is converted to [0]" should read --is converted to [θ]--.

Column 17,
Line 59, "a large quantity of Br" should read --a large quantity of Br⁻--.

Column 18,
Line 47, "NaHCO3 solution" should read --NaHCO$_3$ solution--.

Column 20,
Line 15, "Y 200 GPa for steel," should read --Y ≈ 200 GPa for steel,--.
Line 16, "and -1 GPa for plastics" should read --and ~1 GPa for plastics--.
Line 26, "where I=π R4/4 is" should read --where I = πR⁴/4 is--.

Signed and Sealed this
                  Sixth Day of November, 2018

Andrei Iancu
*Director of the United States Patent and Trademark Office*

Column 22,
Line 27, "stress $\sigma_t$, and" should read --stress $\sigma_b$ and--.
Lines 27-28, "strain $\epsilon_1$, is assessed" should read --strain $\epsilon_b$ is assessed--.

Column 24,
Line 52, "from four 0 strands" should read --from four β strands--.

Column 29,
Line 25, "to form 13 spirals" should read --to form β spirals--.

Column 33,
Line 48, "the –keratin composite:" should read --the α-keratin composite:--.

Column 34,
Line 38, "polymerization of –amino" should read --polymerization of α-amino--.